(12) United States Patent
Davies et al.

(10) Patent No.: US 7,619,069 B2
(45) Date of Patent: Nov. 17, 2009

(54) ANTIBODIES TO TGF-BETA 1

(75) Inventors: Julian Davies, San Diego, CA (US); Craig Duane Dickinson, San Diego, CA (US); David Matthew Marquis, Encinitas, CA (US); Ying Tang, San Diego, CA (US); Peter Edward Vaillancourt, Del Mar, CA (US)

(73) Assignee: Eli Lilly and Company, Indianapolis, IN (US)

( * ) Notice: Subject to any disclaimer, the term of this patent is extended or adjusted under 35 U.S.C. 154(b) by 202 days.

(21) Appl. No.: 11/874,952

(22) Filed: Oct. 19, 2007

(65) Prior Publication Data

US 2008/0050375 A1 Feb. 28, 2008

Related U.S. Application Data

(63) Continuation-in-part of application No. PCT/US2006/014943, filed on Apr. 20, 2006.

(60) Provisional application No. 60/674,082, filed on Apr. 22, 2005.

(51) Int. Cl.
*C07K 16/00* (2006.01)
*A61K 39/395* (2006.01)

(52) U.S. Cl. .................... 530/387.1; 424/130.1

(58) Field of Classification Search .................. None
See application file for complete search history.

(56) References Cited

U.S. PATENT DOCUMENTS

| | | | |
|---|---|---|---|
| 6,492,497 B1 | 12/2002 | Thompson et al. | |
| 6,906,026 B1 | 6/2005 | Noble et al. | |
| 2005/0049403 A1 | 3/2005 | Thompson et al. | |
| 2005/0124534 A1 | 6/2005 | Noble et al. | |
| 2006/0286105 A1 | 12/2006 | Ledbetter et al. | |
| 2007/0148170 A1 | 6/2007 | Desjarlais et al. | |

FOREIGN PATENT DOCUMENTS

| | | |
|---|---|---|
| WO | WO 97/13844 | 4/1997 |
| WO | WO 00/40227 | 7/2000 |
| WO | WO 00/66631 A | 11/2000 |
| WO | WO 2004/098637 | 11/2004 |
| WO | WO 2005/010049 A2 | 2/2005 |
| WO | WO 2005/097832 | 10/2005 |
| WO | WO 2005120437 | 12/2005 |
| WO | WO 2006037029 | 4/2006 |

OTHER PUBLICATIONS

Benigni, et al. "Add-on anti-TGF-beta antibody to ACE inhibitor arrests progressive diabetic nephropathy in the rat." J. Am. Soc. Nephrol. vol. 14 (7) 2003, pp. 1816-1824.
Border, et al., "Suppression of experimental glomerulonephritis by antiserum against transforming growth factor beta 1." Nature, vol. 346 (6282) 1990, pp. 371-374.
Cheng Jingfei et al: "Transforming growth factor-beta signal transduction and progressive rental disease." Experimental Biology and Medicine, vol. 227 (11) 2002, pp. 943-956.
Flanders K C et al: "Antibodies To Peptide Determinants In Transforming Growth Factor Beta And Their Applications" Biochemistry, American Chemical Society, vol. 27, 1988, pp. 739-746.
Lucas C, et al., "The Autocrine Production of Transforming Growth Factor-Beta1 During Lymphocyte Activation a Study With a Monoclonal Antibody-Based Elisa", Journal of Immunology, The Williams and Wilkins Co., vol. 145, 1990, pp. 1415-1422.
Shah, et al., "Neutralisation of TGF-beta1 and TGF-beta2 or exogenous addition of TGF-beta3 to cutaneous rat wounds reduces scarring" J. Cell Science, vol. 108 (Pt 3) 1995, pp. 985-1002.
Shehata Medhat et al., "TGF-beta1 induces bone marrow reticulin fibrosis in hairy cell leukemia," Journal of Clinical Investigation, vol. 113, (5) 2004, pp. 676-685.
Ziyadeh, et al., "Long-term prevention of renal insufficiency, excess matrix gene expression, and glomerular mesangial matrix expansion by treatment with monoclonal antitransforming growth factor-beta antibody in db/db diabetic mice." Proc. Natl. Acad. Sci. U.S.A. vol. 97(14) 2000, pp. 8015-8020.
"Monoclonal anti-TGTF-b1 antibody," R&D System Ordering Information, No. mab2401, Jan. 29, 2003.

*Primary Examiner*—Ilia Ouspenski
(74) *Attorney, Agent, or Firm*—Robert L. Sharp; Charles E. Cohen

(57) ABSTRACT

TGF-beta 1 binding compositions and reagents related thereto are provided. Methods of using such compositions for therapeutic purpose are also provided.

13 Claims, 1 Drawing Sheet

```
                               SEQUENCE LISTING

<160> NUMBER OF SEQ ID NOS: 150

<210> SEQ ID NO 1
<211> LENGTH: 112
<212> TYPE: PRT
<213> ORGANISM: Homo sapiens

<400> SEQUENCE: 1

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 2
<211> LENGTH: 10
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(10)
<223> OTHER INFORMATION: Xaa can be any naturally occurring amino acid

<400> SEQUENCE: 2

Gly Tyr Xaa Phe Xaa Asp Tyr Asn Xaa Xaa
1               5                   10

<210> SEQ ID NO 3
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (1)..(2)
```

```
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 3

Xaa Xaa Tyr Pro Tyr Asp Gly Xaa Thr Gly Xaa Asn Xaa Lys Xaa Lys
1               5                   10                  15

Ser

<210> SEQ ID NO 4
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (4)..(6)
<223> OTHER INFORMATION: Xaa can be any naturally occurring amino acid

<400> SEQUENCE: 4

Gly Tyr Arg Xaa Xaa Xaa Tyr
1               5

<210> SEQ ID NO 5
<211> LENGTH: 10
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 5

Xaa Ala Xaa Xaa Xaa Val Xaa Tyr Met His
1               5                   10

<210> SEQ ID NO 6
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (5)..(5)
<223> OTHER INFORMATION: Xaa can be any naturally occurring amino acid
<220> FEATURE:
```

```
<221> NAME/KEY: misc_feature
<222> LOCATION: (7)..(7)
<223> OTHER INFORMATION: Xaa can be any naturally occurring amino acid

<400> SEQUENCE: 6

Ala Thr Ser Asn Xaa Ala Xaa
1               5

<210> SEQ ID NO 7
<211> LENGTH: 9
<212> TYPE: PRT
<213> ORGANISM: Artificial
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid

<400> SEQUENCE: 7

Xaa Gln Trp Asp Xaa Xaa Xaa Pro Ala
1               5

<210> SEQ ID NO 8
<211> LENGTH: 25
<212> TYPE: PRT
<213> ORGANISM: Homo sapiens

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 9
<211> LENGTH: 14
<212> TYPE: PRT
<213> ORGANISM: Homo sapiens

<400> SEQUENCE: 9

Trp Val Arg Gln Ala Pro Gly Gln Gly Leu Glu Trp Met Gly
1               5                   10

<210> SEQ ID NO 10
<211> LENGTH: 32
<212> TYPE: PRT
<213> ORGANISM: Homo sapiens

<400> SEQUENCE: 10

Arg Val Thr Met Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 11
<211> LENGTH: 11
<212> TYPE: PRT
<213> ORGANISM: Homo sapiens

<400> SEQUENCE: 11

Trp Gly Gln Gly Thr Leu Val Thr Val Ser Ser
1               5                   10
```

```
<210> SEQ ID NO 12
<211> LENGTH: 23
<212> TYPE: PRT
<213> ORGANISM: Homo sapiens

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 13
<211> LENGTH: 15
<212> TYPE: PRT
<213> ORGANISM: Homo sapiens

<400> SEQUENCE: 13

Trp Tyr Gln Gln Lys Pro Gly Lys Ala Pro Lys Pro Leu Ile Tyr
1               5                   10                  15

<210> SEQ ID NO 14
<211> LENGTH: 15
<212> TYPE: PRT
<213> ORGANISM: Homo sapiens

<400> SEQUENCE: 14

Trp Tyr Gln Gln Lys Pro Gly Lys Ala Pro Lys Leu Leu Ile Tyr
1               5                   10                  15

<210> SEQ ID NO 15
<211> LENGTH: 15
<212> TYPE: PRT
<213> ORGANISM: Homo sapiens

<400> SEQUENCE: 15

Trp Tyr Gln Gln Lys Pro Gly Lys Ala Pro Lys Ser Leu Ile Tyr
1               5                   10                  15

<210> SEQ ID NO 16
<211> LENGTH: 15
<212> TYPE: PRT
<213> ORGANISM: Homo sapiens

<400> SEQUENCE: 16

Trp Tyr Gln Gln Lys Pro Glu Lys Ala Pro Lys Pro Leu Ile Tyr
1               5                   10                  15

<210> SEQ ID NO 17
<211> LENGTH: 15
<212> TYPE: PRT
<213> ORGANISM: Homo sapiens

<400> SEQUENCE: 17

Trp Tyr Gln Gln Lys Pro Glu Lys Ala Pro Lys Leu Leu Ile Tyr
1               5                   10                  15

<210> SEQ ID NO 18
<211> LENGTH: 15
<212> TYPE: PRT
<213> ORGANISM: Homo sapiens

<400> SEQUENCE: 18

Trp Tyr Gln Gln Lys Pro Glu Lys Ala Pro Lys Ser Leu Ile Tyr
```

```
1               5                  10                 15
```

<210> SEQ ID NO 19
<211> LENGTH: 15
<212> TYPE: PRT
<213> ORGANISM: Homo sapiens

<400> SEQUENCE: 19

```
Trp Phe Gln Gln Lys Pro Gly Lys Ala Pro Lys Pro Leu Ile Tyr
1               5                  10                 15
```

<210> SEQ ID NO 20
<211> LENGTH: 15
<212> TYPE: PRT
<213> ORGANISM: Homo sapiens

<400> SEQUENCE: 20

```
Trp Phe Gln Gln Lys Pro Gly Lys Ala Pro Lys Leu Leu Ile Tyr
1               5                  10                 15
```

<210> SEQ ID NO 21
<211> LENGTH: 15
<212> TYPE: PRT
<213> ORGANISM: Homo sapiens

<400> SEQUENCE: 21

```
Trp Phe Gln Gln Lys Pro Gly Lys Ala Pro Lys Ser Leu Ile Tyr
1               5                  10                 15
```

<210> SEQ ID NO 22
<211> LENGTH: 15
<212> TYPE: PRT
<213> ORGANISM: Homo sapiens

<400> SEQUENCE: 22

```
Trp Phe Gln Gln Lys Pro Glu Lys Ala Pro Lys Pro Leu Ile Tyr
1               5                  10                 15
```

<210> SEQ ID NO 23
<211> LENGTH: 15
<212> TYPE: PRT
<213> ORGANISM: Homo sapiens

<400> SEQUENCE: 23

```
Trp Phe Gln Gln Lys Pro Glu Lys Ala Pro Lys Leu Leu Ile Tyr
1               5                  10                 15
```

<210> SEQ ID NO 24
<211> LENGTH: 15
<212> TYPE: PRT
<213> ORGANISM: Homo sapiens

<400> SEQUENCE: 24

```
Trp Phe Gln Gln Lys Pro Glu Lys Ala Pro Lys Ser Leu Ile Tyr
1               5                  10                 15
```

<210> SEQ ID NO 25
<211> LENGTH: 15
<212> TYPE: PRT
<213> ORGANISM: Homo sapiens

<400> SEQUENCE: 25

```
Trp Tyr Gln Gln Lys Pro Gly Lys Ala Pro Lys Pro Trp Ile Tyr
1               5                  10                 15
```

```
<210> SEQ ID NO 26
<211> LENGTH: 15
<212> TYPE: PRT
<213> ORGANISM: Homo sapiens

<400> SEQUENCE: 26

Trp Tyr Gln Gln Lys Pro Gly Lys Ala Pro Lys Leu Trp Ile Tyr
1               5                   10                  15

<210> SEQ ID NO 27
<211> LENGTH: 15
<212> TYPE: PRT
<213> ORGANISM: Homo sapiens

<400> SEQUENCE: 27

Trp Tyr Gln Gln Lys Pro Gly Lys Ala Pro Lys Ser Trp Ile Tyr
1               5                   10                  15

<210> SEQ ID NO 28
<211> LENGTH: 15
<212> TYPE: PRT
<213> ORGANISM: Homo sapiens

<400> SEQUENCE: 28

Trp Tyr Gln Gln Lys Pro Glu Lys Ala Pro Lys Pro Trp Ile Tyr
1               5                   10                  15

<210> SEQ ID NO 29
<211> LENGTH: 15
<212> TYPE: PRT
<213> ORGANISM: Homo sapiens

<400> SEQUENCE: 29

Trp Tyr Gln Gln Lys Pro Glu Lys Ala Pro Lys Leu Trp Ile Tyr
1               5                   10                  15

<210> SEQ ID NO 30
<211> LENGTH: 15
<212> TYPE: PRT
<213> ORGANISM: Homo sapiens

<400> SEQUENCE: 30

Trp Tyr Gln Gln Lys Pro Glu Lys Ala Pro Lys Ser Trp Ile Tyr
1               5                   10                  15

<210> SEQ ID NO 31
<211> LENGTH: 15
<212> TYPE: PRT
<213> ORGANISM: Homo sapiens

<400> SEQUENCE: 31

Trp Phe Gln Gln Lys Pro Gly Lys Ala Pro Lys Pro Trp Ile Tyr
1               5                   10                  15

<210> SEQ ID NO 32
<211> LENGTH: 15
<212> TYPE: PRT
<213> ORGANISM: Homo sapiens

<400> SEQUENCE: 32

Trp Phe Gln Gln Lys Pro Gly Lys Ala Pro Lys Leu Trp Ile Tyr
1               5                   10                  15

<210> SEQ ID NO 33
```

```
<211> LENGTH: 15
<212> TYPE: PRT
<213> ORGANISM: Homo sapiens

<400> SEQUENCE: 33

Trp Phe Gln Gln Lys Pro Gly Lys Ala Pro Lys Ser Trp Ile Tyr
1               5                   10                  15

<210> SEQ ID NO 34
<211> LENGTH: 15
<212> TYPE: PRT
<213> ORGANISM: Homo sapiens

<400> SEQUENCE: 34

Trp Phe Gln Gln Lys Pro Glu Lys Ala Pro Lys Pro Trp Ile Tyr
1               5                   10                  15

<210> SEQ ID NO 35
<211> LENGTH: 15
<212> TYPE: PRT
<213> ORGANISM: Homo sapiens

<400> SEQUENCE: 35

Trp Phe Gln Gln Lys Pro Glu Lys Ala Pro Lys Leu Trp Ile Tyr
1               5                   10                  15

<210> SEQ ID NO 36
<211> LENGTH: 15
<212> TYPE: PRT
<213> ORGANISM: Homo sapiens

<400> SEQUENCE: 36

Trp Phe Gln Gln Lys Pro Glu Lys Ala Pro Lys Ser Trp Ile Tyr
1               5                   10                  15

<210> SEQ ID NO 37
<211> LENGTH: 32
<212> TYPE: PRT
<213> ORGANISM: Homo sapiens

<400> SEQUENCE: 37

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 38
<211> LENGTH: 10
<212> TYPE: PRT
<213> ORGANISM: Homo sapiens

<400> SEQUENCE: 38

Phe Gly Gln Gly Thr Lys Leu Glu Ile Lys
1               5                   10

<210> SEQ ID NO 39
<211> LENGTH: 328
<212> TYPE: PRT
<213> ORGANISM: Homo sapiens

<400> SEQUENCE: 39

Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
```

```
                  20                  25                  30
Pro Glu Pro Val Thr Val Ser Trp Asn Ser Gly Ala Leu Thr Ser Gly
            35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Lys Val Asp Lys Lys
                    85                  90                  95

Val Glu Pro Lys Ser Cys Asp Lys Thr His Thr Cys Pro Pro Cys Pro
                100                 105                 110

Ala Pro Glu Leu Leu Gly Gly Pro Ser Val Phe Leu Phe Pro Pro Lys
            115                 120                 125

Pro Lys Asp Thr Leu Met Ile Ser Arg Thr Pro Glu Val Thr Cys Val
            130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
                180                 185                 190

Gln Asp Trp Leu Asn Gly Lys Glu Tyr Lys Cys Lys Val Ser Asn Lys
            195                 200                 205

Ala Leu Pro Ala Pro Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
                260                 265                 270

Tyr Lys Thr Thr Pro Pro Val Leu Asp Ser Asp Gly Ser Phe Phe Leu
            275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly
                325

<210> SEQ ID NO 40
<211> LENGTH: 326
<212> TYPE: PRT
<213> ORGANISM: Homo sapiens

<400> SEQUENCE: 40

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60
```

```
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
            325

<210> SEQ ID NO 41
<211> LENGTH: 107
<212> TYPE: PRT
<213> ORGANISM: Homo sapiens

<400> SEQUENCE: 41

Arg Thr Val Ala Ala Pro Ser Val Phe Ile Phe Pro Pro Ser Asp Glu
 1                5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 42
<211> LENGTH: 106
<212> TYPE: PRT
<213> ORGANISM: Artificial
<220> FEATURE:
<223> OTHER INFORMATION: Synthetic construct

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Pro Leu Ile Tyr
        35                  40                  45

Ala Thr Ser Asn Leu Ala Lys Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 43
<211> LENGTH: 106
<212> TYPE: PRT
<213> ORGANISM: Artificial
<220> FEATURE:
<223> OTHER INFORMATION: Synthetic construct

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Pro Leu Ile Tyr
        35                  40                  45

Ala Thr Ser Asn Leu Ala Tyr Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 44
<211> LENGTH: 106
<212> TYPE: PRT
<213> ORGANISM: Artificial
<220> FEATURE:
<223> OTHER INFORMATION: Synthetic construct

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Pro Leu Ile Tyr
        35                  40                  45

Ala Thr Ser Asn Leu Ala Leu Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 45
<211> LENGTH: 106
<212> TYPE: PRT
<213> ORGANISM: Artificial
<220> FEATURE:
<223> OTHER INFORMATION: Synthetic construct

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Leu Val Ser Tyr Met
            20                  25                  30

His Trp Tyr Gln Gln Lys Pro Gly Lys Ala Pro Lys Pro Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 46
<211> LENGTH: 106
<212> TYPE: PRT
<213> ORGANISM: Artificial
<220> FEATURE:
<223> OTHER INFORMATION: Synthetic construct

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Tyr Ala Ser Ser Ser Val Ser Tyr Met
            20                  25                  30

His Trp Tyr Gln Gln Lys Pro Gly Lys Ala Pro Lys Pro Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 47

<211> LENGTH: 106
<212> TYPE: PRT
<213> ORGANISM: Artificial
<220> FEATURE:
<223> OTHER INFORMATION: Synthetic construct

<400> SEQUENCE: 47

```
Asp Ile Gln Met Thr Gln Ser Pro Ser Ser Leu Ser Ala Ser Val Gly
1               5                   10                  15

Asp Arg Val Thr Ile Thr Cys Glu Ala Ser Ser Val Ser Tyr Met
            20                  25                  30

His Trp Tyr Gln Gln Lys Pro Gly Lys Ala Pro Lys Pro Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105
```

<210> SEQ ID NO 48
<211> LENGTH: 106
<212> TYPE: PRT
<213> ORGANISM: Artificial
<220> FEATURE:
<223> OTHER INFORMATION: Synthetic construct

<400> SEQUENCE: 48

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Ser Val Ser Tyr Met
            20                  25                  30

His Trp Tyr Gln Gln Lys Pro Gly Lys Ala Pro Lys Pro Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105
```

<210> SEQ ID NO 49
<211> LENGTH: 106
<212> TYPE: PRT
<213> ORGANISM: Artificial
<220> FEATURE:
<223> OTHER INFORMATION: Synthetic construct

<400> SEQUENCE: 49

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Pro Leu Ile Tyr
        35                  40                  45
```

Ala Thr Ser Asn Asn Ala Ser Gly Val Pro Ser Arg Phe Gly Ser
            50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 50
<211> LENGTH: 106
<212> TYPE: PRT
<213> ORGANISM: Homo sapiens

<400> SEQUENCE: 50

Asp Ile Gln Met Thr Gln Ser Pro Ser Ser Leu Ser Ala Ser Val Gly
 1               5                  10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Pro Leu Ile Tyr
            35                  40                  45

Ala Thr Ser Asn Leu Ala Met Gly Val Pro Ser Arg Phe Ser Gly Ser
            50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 51
<211> LENGTH: 106
<212> TYPE: PRT
<213> ORGANISM: Artificial
<220> FEATURE:
<223> OTHER INFORMATION: Synthetic construct

<400> SEQUENCE: 51

Asp Ile Gln Met Thr Gln Ser Pro Ser Ser Leu Ser Ala Ser Val Gly
 1               5                  10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Pro Leu Ile Tyr
            35                  40                  45

Ala Thr Ser Asn Leu Ala Ser Gly Val Pro Ser Arg Phe Ser Gly Ser
            50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 52
<211> LENGTH: 106
<212> TYPE: PRT
<213> ORGANISM: Artificial
<220> FEATURE:
<223> OTHER INFORMATION: Synthetic construct

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Pro Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Phe Pro Ala
                85                  90                  95

Phe Gly Gln Gly Thr Lys Leu Glu Ile Lys
            100                 105

<210> SEQ ID NO 53
<211> LENGTH: 106
<212> TYPE: PRT
<213> ORGANISM: Artificial
<220> FEATURE:
<223> OTHER INFORMATION: Synthetic construct

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Pro Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Asp Asn Pro Pro Ala
                85                  90                  95

Phe Gly Gln Gly Thr Lys Leu Glu Ile Lys
            100                 105

<210> SEQ ID NO 54
<211> LENGTH: 106
<212> TYPE: PRT
<213> ORGANISM: Artificial
<220> FEATURE:
<223> OTHER INFORMATION: Synthetic construct

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Pro Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

```
Asp Phe Ala Thr Tyr Tyr Cys Gln Gln Trp Asp Leu Arg Pro Pro Ala
                85                  90                  95

Phe Gly Gln Gly Thr Lys Leu Glu Ile Lys
            100                 105

<210> SEQ ID NO 55
<211> LENGTH: 106
<212> TYPE: PRT
<213> ORGANISM: Homo sapiens

<400> SEQUENCE: 55

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Pro Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Ser Gln Trp Asp Leu Asn Pro Pro Ala
                85                  90                  95

Phe Gly Gln Gly Thr Lys Leu Glu Ile Lys
            100                 105

<210> SEQ ID NO 56
<211> LENGTH: 106
<212> TYPE: PRT
<213> ORGANISM: Artificial
<220> FEATURE:
<223> OTHER INFORMATION: Synthetic construct

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Pro Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Tyr Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 57
<211> LENGTH: 106
<212> TYPE: PRT
<213> ORGANISM: Artificial
<220> FEATURE:
<223> OTHER INFORMATION: Synthetic construct

<400> SEQUENCE: 57

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Ser Ser Val Pro Tyr Met
            20                  25                  30

His Trp Tyr Gln Gln Lys Pro Gly Lys Ala Pro Lys Leu Leu Ile Tyr
        35                  40                  45

Ala Thr Ser Asn Pro Ala Tyr Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 58
<211> LENGTH: 106
<212> TYPE: PRT
<213> ORGANISM: Artificial
<220> FEATURE:
<223> OTHER INFORMATION: Synthetic construct

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Pro Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 59
<211> LENGTH: 106
<212> TYPE: PRT
<213> ORGANISM: Artificial
<220> FEATURE:
<223> OTHER INFORMATION: Synthetic construct

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Pro Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
```

<210> SEQ ID NO 60
<211> LENGTH: 106
<212> TYPE: PRT
<213> ORGANISM: Artificial
<220> FEATURE:
<223> OTHER INFORMATION: Synthetic construct

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Pro Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Lys Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 61
<211> LENGTH: 106
<212> TYPE: PRT
<213> ORGANISM: Artificial
<220> FEATURE:
<223> OTHER INFORMATION: Synthetic construct

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Pro Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Phe Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 62
<211> LENGTH: 106
<212> TYPE: PRT
<213> ORGANISM: Artificial
<220> FEATURE:
<223> OTHER INFORMATION: Synthetic construct

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Val Ser Val Ser Tyr Met
            20                  25                  30

His Trp Tyr Gln Gln Lys Pro Gly Lys Ala Pro Lys Leu Leu Ile Tyr
            35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 63
<211> LENGTH: 106
<212> TYPE: PRT
<213> ORGANISM: Artificial
<220> FEATURE:
<223> OTHER INFORMATION: Synthetic construct

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Leu Tyr Met
            20                  25                  30

His Trp Tyr Gln Gln Lys Pro Gly Lys Ala Pro Lys Leu Leu Ile Tyr
            35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 64
<211> LENGTH: 106
<212> TYPE: PRT
<213> ORGANISM: Artificial
<220> FEATURE:
<223> OTHER INFORMATION: Synthetic construct

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Thr Ser Ser Val Leu Tyr Met
            20                  25                  30

His Trp Tyr Gln Gln Lys Pro Gly Lys Ala Pro Lys Leu Leu Ile Tyr
            35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

```
<210> SEQ ID NO 65
<211> LENGTH: 106
<212> TYPE: PRT
<213> ORGANISM: Artificial
<220> FEATURE:
<223> OTHER INFORMATION: Synthetic construct

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Tyr Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 66
<211> LENGTH: 106
<212> TYPE: PRT
<213> ORGANISM: Artificial
<220> FEATURE:
<223> OTHER INFORMATION: Synthetic construct

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Glu Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 67
<211> LENGTH: 106
<212> TYPE: PRT
<213> ORGANISM: Artificial
<220> FEATURE:
<223> OTHER INFORMATION: Synthetic construct

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Leu Leu Ile Tyr
        35                  40                  45
```

-continued

Ala Thr Ser Asn Leu Ala Gln Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 68
<211> LENGTH: 106
<212> TYPE: PRT
<213> ORGANISM: Artificial
<220> FEATURE:
<223> OTHER INFORMATION: Synthetic construct

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Tyr Pro Ala
                85                  90                  95

Phe Gly Gln Gly Thr Lys Leu Glu Ile Lys
            100                 105

<210> SEQ ID NO 69
<211> LENGTH: 106
<212> TYPE: PRT
<213> ORGANISM: Artificial
<220> FEATURE:
<223> OTHER INFORMATION: Synthetic construct

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Gly Lys Ala Pro Lys Leu Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 70
<211> LENGTH: 106
<212> TYPE: PRT

```
<213> ORGANISM: Artificial
<220> FEATURE:
<223> OTHER INFORMATION: Synthetic construct

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Pro Tyr Met
            20                  25                  30

His Trp Tyr Gln Gln Lys Pro Glu Lys Ala Pro Lys Ser Leu Ile Tyr
        35                  40                  45

Ala Thr Ser Asn Leu Ala Tyr Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 71
<211> LENGTH: 106
<212> TYPE: PRT
<213> ORGANISM: Artificial
<220> FEATURE:
<223> OTHER INFORMATION: Synthetic construct

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Pro Tyr Met
            20                  25                  30

His Trp Tyr Gln Gln Lys Pro Glu Lys Ala Pro Lys Ser Leu Ile Tyr
        35                  40                  45

Ala Thr Ser Asn Leu Ala Leu Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 72
<211> LENGTH: 106
<212> TYPE: PRT
<213> ORGANISM: Artificial
<220> FEATURE:
<223> OTHER INFORMATION: Synthetic construct

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Pro Tyr Met
            20                  25                  30

His Trp Tyr Gln Gln Lys Pro Glu Lys Ala Pro Lys Ser Leu Ile Tyr
        35                  40                  45

Ala Thr Ser Asn Leu Ala Lys Gly Val Pro Ser Arg Phe Ser Gly Ser
    50                  55                  60
```

```
Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Asp Leu Asn Pro Pro Ala
                 85                  90                  95

Phe Gly Gln Gly Thr Lys Leu Glu Ile Lys
            100                 105

<210> SEQ ID NO 73
<211> LENGTH: 106
<212> TYPE: PRT
<213> ORGANISM: Artificial
<220> FEATURE:
<223> OTHER INFORMATION: Synthetic construct

<400> SEQUENCE: 73

Asp Ile Gln Met Thr Gln Ser Pro Ser Ser Leu Ser Ala Ser Val Gly
  1               5                  10                  15

Asp Arg Val Thr Ile Thr Cys Arg Ala Ser Ser Val Pro Tyr Met
                 20                  25                  30

His Trp Tyr Gln Gln Lys Pro Glu Lys Ala Pro Lys Ser Leu Ile Tyr
             35                  40                  45

Ala Thr Ser Asn Leu Ala Phe Gly Val Pro Ser Arg Phe Ser Gly Ser
         50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Asp Leu Asn Pro Pro Ala
                 85                  90                  95

Phe Gly Gln Gly Thr Lys Leu Glu Ile Lys
            100                 105

<210> SEQ ID NO 74
<211> LENGTH: 106
<212> TYPE: PRT
<213> ORGANISM: Artificial
<220> FEATURE:
<223> OTHER INFORMATION: Synthetic construct

<400> SEQUENCE: 74

Asp Ile Gln Met Thr Gln Ser Pro Ser Ser Leu Ser Ala Ser Val Gly
  1               5                  10                  15

Asp Arg Val Thr Ile Thr Cys Arg Ala Ser Ala Ser Val Pro Tyr Met
                 20                  25                  30

His Trp Tyr Gln Gln Lys Pro Glu Lys Ala Pro Lys Ser Leu Ile Tyr
             35                  40                  45

Ala Thr Ser Asn Leu Ala Lys Gly Val Pro Ser Arg Phe Ser Gly Ser
         50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Asp Leu Asn Pro Pro Ala
                 85                  90                  95

Phe Gly Gln Gly Thr Lys Leu Glu Ile Lys
            100                 105

<210> SEQ ID NO 75
<211> LENGTH: 106
<212> TYPE: PRT
<213> ORGANISM: Artificial
<220> FEATURE:
<223> OTHER INFORMATION: Synthetic construct
```

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Arg Ala Ser Ala Ser Val Pro Tyr Met
            20                  25                  30

His Trp Tyr Gln Gln Lys Pro Glu Lys Ala Pro Lys Ser Leu Ile Tyr
        35                  40                  45

Ala Thr Ser Asn Leu Ala Tyr Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 76
<211> LENGTH: 106
<212> TYPE: PRT
<213> ORGANISM: Artificial
<220> FEATURE:
<223> OTHER INFORMATION: Synthetic construct

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Arg Ala Arg Ser Ser Val Ser Tyr Met
            20                  25                  30

His Trp Tyr Gln Gln Lys Pro Glu Lys Ala Pro Lys Ser Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 77
<211> LENGTH: 106
<212> TYPE: PRT
<213> ORGANISM: Artificial
<220> FEATURE:
<223> OTHER INFORMATION: Synthetic construct

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Ser Tyr Met
            20                  25                  30

His Trp Tyr Gln Gln Lys Pro Glu Lys Ala Pro Lys Ser Leu Ile Tyr
        35                  40                  45

Ala Thr Ser Asn Leu Ala Arg Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 78
<211> LENGTH: 106
<212> TYPE: PRT
<213> ORGANISM: Artificial
<220> FEATURE:
<223> OTHER INFORMATION: Synthetic construct

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Glu Lys Ala Pro Lys Ser Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Arg Pro Ala
                85                  90                  95

Phe Gly Gln Gly Thr Lys Leu Glu Ile Lys
            100                 105

<210> SEQ ID NO 79
<211> LENGTH: 106
<212> TYPE: PRT
<213> ORGANISM: Artificial
<220> FEATURE:
<223> OTHER INFORMATION: Synthetic construct

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Glu Lys Ala Pro Lys Ser Leu Ile Tyr
        35                  40                  45

Ala Thr Ser Asn Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Pro Asn Pro Pro Ala
                85                  90                  95

Phe Gly Gln Gly Thr Lys Leu Glu Ile Lys
            100                 105

<210> SEQ ID NO 80
<211> LENGTH: 106
<212> TYPE: PRT
<213> ORGANISM: Artificial
<220> FEATURE:
<223> OTHER INFORMATION: Synthetic construct

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Glu Lys Ala Pro Lys Ser Leu Ile Tyr
            35                  40                  45

Ala Thr Ser Asn Leu Ala Ser Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 81
<211> LENGTH: 106
<212> TYPE: PRT
<213> ORGANISM: Artificial
<220> FEATURE:
<223> OTHER INFORMATION: Synthetic construct

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Pro Tyr Met
            20                  25                  30

His Trp Phe Gln Gln Lys Pro Glu Lys Ala Pro Lys Ser Leu Ile Tyr
            35                  40                  45

Ala Thr Ser Asn Leu Ala Phe Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 82
<211> LENGTH: 106
<212> TYPE: PRT
<213> ORGANISM: Artificial
<220> FEATURE:
<223> OTHER INFORMATION: Synthetic construct

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Pro Tyr Met
            20                  25                  30

His Trp Phe Gln Gln Lys Pro Glu Lys Ala Pro Lys Ser Leu Ile Tyr
            35                  40                  45

Ala Thr Ser Asn Leu Ala Tyr Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

```
Phe Gly Gln Gly Thr Lys Leu Glu Ile Lys
            100                 105

<210> SEQ ID NO 83
<211> LENGTH: 106
<212> TYPE: PRT
<213> ORGANISM: Artificial
<220> FEATURE:
<223> OTHER INFORMATION: Synthetic construct

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Pro Tyr Met
            20                  25                  30

His Trp Phe Gln Gln Lys Pro Glu Lys Ala Pro Lys Ser Leu Ile Tyr
            35                  40                  45

Ala Thr Ser Asn Leu Ala Leu Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 84
<211> LENGTH: 106
<212> TYPE: PRT
<213> ORGANISM: Artificial
<220> FEATURE:
<223> OTHER INFORMATION: Synthetic construct

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Pro Tyr Met
            20                  25                  30

His Trp Phe Gln Gln Lys Pro Glu Lys Ala Pro Lys Ser Leu Ile Tyr
            35                  40                  45

Ala Thr Ser Asn Leu Ala His Gly Val Pro Ser Arg Phe Ser Gly Ser
        50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 85
<211> LENGTH: 106
<212> TYPE: PRT
<213> ORGANISM: Artificial
<220> FEATURE:
<223> OTHER INFORMATION: Synthetic construct

<400> SEQUENCE: 85

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Ser Val Pro Tyr Met
            20                  25                  30

His Trp Phe Gln Gln Lys Pro Glu Lys Ala Pro Lys Ser Leu Ile Tyr
        35                  40                  45

Ala Thr Ser Asn Leu Ala Lys Gly Val Pro Ser Arg Phe Ser Gly Ser
 50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 86
<211> LENGTH: 106
<212> TYPE: PRT
<213> ORGANISM: Artificial
<220> FEATURE:
<223> OTHER INFORMATION: Synthetic construct

<400> SEQUENCE: 86

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Pro Tyr Met
            20                  25                  30

His Trp Phe Gln Gln Lys Pro Glu Lys Ala Pro Lys Ser Leu Ile Tyr
        35                  40                  45

Ala Thr Ser Asn Pro Ala Tyr Gly Val Pro Ser Arg Phe Ser Gly Ser
 50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 87
<211> LENGTH: 116
<212> TYPE: PRT
<213> ORGANISM: Artificial
<220> FEATURE:
<223> OTHER INFORMATION: Synthetic construct

<400> SEQUENCE: 87

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Glu Asp Tyr
            20                  25                  30

Asn Met His Trp Val Arg Gln Ala Pro Gly Gln Gly Leu Glu Trp Met
        35                  40                  45

Gly Tyr Ile Tyr Pro Tyr Asp Gly Glu Thr Gly Tyr Asn Gln Lys Phe
 50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Arg Trp Leu Ala Tyr Trp Gly Gln Gly Thr Leu Val
            100                 105                 110

Thr Val Ser Ser
        115

<210> SEQ ID NO 88
<211> LENGTH: 116
<212> TYPE: PRT
<213> ORGANISM: Artificial
<220> FEATURE:
<223> OTHER INFORMATION: Synthetic construct

<400> SEQUENCE: 88

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Thr Asp Tyr
            20                  25                  30

Asn Met His Trp Val Arg Gln Ala Pro Gly Gln Gly Leu Glu Trp Met
        35                  40                  45

Gly Tyr Ile Tyr Pro Tyr Asp Gly Glu Thr Gly Tyr Asn Gln Lys Phe
    50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Arg Trp Phe Ala Tyr Trp Gly Gln Gly Thr Leu Val
            100                 105                 110

Thr Val Ser Ser
        115

<210> SEQ ID NO 89
<211> LENGTH: 115
<212> TYPE: PRT
<213> ORGANISM: Artificial
<220> FEATURE:
<223> OTHER INFORMATION: Synthetic construct

<400> SEQUENCE: 89

Val Gln Leu Val Gln Ser Gly Ala Glu Val Lys Lys Pro Gly Ala Ser
1               5                   10                  15

Val Lys Val Ser Cys Lys Ala Ser Gly Tyr Asp Phe Thr Asp Tyr Asn
            20                  25                  30

Ile His Trp Val Arg Gln Ala Pro Gly Gln Gly Leu Glu Trp Met Gly
        35                  40                  45

Tyr Ile Tyr Pro Tyr Asp Gly Glu Thr Gly Tyr Asn Gln Lys Phe Lys
    50                  55                  60

Ser Arg Val Thr Met Thr Thr Asp Thr Ser Thr Ser Thr Ala Tyr Met
65                  70                  75                  80

Glu Leu Arg Ser Leu Arg Ser Asp Asp Thr Ala Val Tyr Tyr Cys Ala
                85                  90                  95

Arg Gly Tyr Arg Trp Phe Ala Tyr Trp Gly Gln Gly Thr Leu Val Thr
            100                 105                 110

Val Ser Ser
        115

<210> SEQ ID NO 90
<211> LENGTH: 116
<212> TYPE: PRT
<213> ORGANISM: Artificial
<220> FEATURE:
<223> OTHER INFORMATION: Synthetic construct

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Thr Asp Tyr
            20                  25                  30

Asn Ile His Trp Val Arg Gln Ala Pro Gly Gln Gly Leu Glu Trp Met
        35                  40                  45

Gly Tyr Ile Tyr Pro Tyr Asp Gly Glu Thr Gly Tyr Asn Gln Lys Phe
    50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Arg Trp Leu Ala Tyr Trp Gly Gln Gly Thr Leu Val
            100                 105                 110

Thr Val Ser Ser
        115

<210> SEQ ID NO 91
<211> LENGTH: 116
<212> TYPE: PRT
<213> ORGANISM: Artificial
<220> FEATURE:
<223> OTHER INFORMATION: Synthetic construct

<400> SEQUENCE: 91

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Glu Asp Tyr
            20                  25                  30

Asn Met His Trp Val Arg Gln Ala Pro Gly Gln Gly Leu Glu Trp Met
        35                  40                  45

Gly Tyr Ile Tyr Pro Tyr Asp Gly Glu Thr Gly Tyr Asn Gln Lys Phe
    50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Arg Trp Phe Ala Tyr Trp Gly Gln Gly Thr Leu Val
            100                 105                 110

Thr Val Ser Ser
        115

<210> SEQ ID NO 92
<211> LENGTH: 116
<212> TYPE: PRT
<213> ORGANISM: Artificial
<220> FEATURE:
<223> OTHER INFORMATION: Synthetic construct

<400> SEQUENCE: 92

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Thr Asp Tyr
            20                  25                  30

Asn Met His Trp Val Arg Gln Ala Pro Gly Gln Gly Leu Glu Trp Met
        35                  40                  45

Gly Tyr Ile Tyr Pro Tyr Asp Gly Glu Thr Gly Tyr Asn Gln Lys Phe
            50                  55                  60

Lys Ser Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Tyr Arg Trp Leu Tyr Tyr Trp Gly Gln Gly Thr Leu Val
            100                 105                 110

Thr Val Ser Ser
        115

<210> SEQ ID NO 93
<211> LENGTH: 116
<212> TYPE: PRT
<213> ORGANISM: Artificial
<220> FEATURE:
<223> OTHER INFORMATION: Synthetic construct

<400> SEQUENCE: 93

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Glu Asp Tyr
             20                  25                  30

Asn Ile His Trp Val Arg Gln Ala Pro Gly Gln Gly Leu Glu Trp Met
         35                  40                  45

Gly Tyr Ile Tyr Pro Tyr Asp Gly Glu Thr Gly Tyr Asn Gln Lys Phe
            50                  55                  60

Lys Ser Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Tyr Arg Trp Phe Ala Tyr Trp Gly Gln Gly Thr Leu Val
            100                 105                 110

Thr Val Ser Ser
        115

<210> SEQ ID NO 94
<211> LENGTH: 116
<212> TYPE: PRT
<213> ORGANISM: Artificial
<220> FEATURE:
<223> OTHER INFORMATION: Synthetic construct

<400> SEQUENCE: 94

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Asp Phe Thr Asp Tyr
             20                  25                  30

Asn Leu His Trp Val Arg Gln Ala Pro Gly Gln Gly Leu Glu Trp Met
         35                  40                  45

Gly Tyr Ile Tyr Pro Tyr Asp Gly Glu Thr Gly Tyr Asn Gln Lys Phe
            50                  55                  60

Lys Ser Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Tyr Arg Trp Leu Ala Tyr Trp Gly Gln Gly Thr Leu Val

```
                      100                 105                 110

Thr Val Ser Ser
        115

<210> SEQ ID NO 95
<211> LENGTH: 116
<212> TYPE: PRT
<213> ORGANISM: Artificial
<220> FEATURE:
<223> OTHER INFORMATION: Synthetic construct

<400> SEQUENCE: 95

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Thr Asp Tyr
            20                  25                  30

Asn Leu His Trp Val Arg Gln Ala Pro Gly Gln Gly Leu Glu Trp Met
        35                  40                  45

Gly Tyr Ile Tyr Pro Tyr Asp Gly Glu Thr Gly Tyr Asn Gln Lys Phe
    50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Arg Trp Phe Ala Tyr Trp Gly Gln Gly Thr Leu Val
            100                 105                 110

Thr Val Ser Ser
        115

<210> SEQ ID NO 96
<211> LENGTH: 116
<212> TYPE: PRT
<213> ORGANISM: Artificial
<220> FEATURE:
<223> OTHER INFORMATION: Synthetic construct

<400> SEQUENCE: 96

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Met
        35                  40                  45

Gly Tyr Ile Tyr Pro Tyr Asp Gly Asp Thr Gly Tyr Asn Gln Lys Phe
    50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Arg Trp Phe Ala Tyr Trp Gly Gln Gly Thr Leu Val
            100                 105                 110

Thr Val Ser Ser
        115

<210> SEQ ID NO 97
<211> LENGTH: 116
<212> TYPE: PRT
<213> ORGANISM: Artificial
<220> FEATURE:
```

<223> OTHER INFORMATION: Synthetic construct

<400> SEQUENCE: 97

| Gln | Val | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Thr | Phe | Thr | Asp | Tyr |
|---|---|---|---|---|---|---|---|---|---|---|---|---|---|---|---|
| | | | 20 | | | | | 25 | | | | | 30 | | |

| Asn | Met | His | Trp | Val | Arg | Gln | Ala | Pro | Gly | Gln | Gly | Leu | Glu | Trp | Met |
|---|---|---|---|---|---|---|---|---|---|---|---|---|---|---|---|
| | | 35 | | | | | 40 | | | | | 45 | | | |

| Gly | Tyr | Val | Tyr | Pro | Tyr | Asp | Gly | Asp | Thr | Gly | Tyr | Asn | Gln | Lys | Phe |
|---|---|---|---|---|---|---|---|---|---|---|---|---|---|---|---|
| | 50 | | | | | 55 | | | | | 60 | | | | |

| Lys | Ser | Arg | Val | Thr | Met | Thr | Thr | Asp | Thr | Ser | Thr | Ser | Thr | Ala | Tyr |
|---|---|---|---|---|---|---|---|---|---|---|---|---|---|---|---|
| 65 | | | | | 70 | | | | | 75 | | | | | 80 |

| Met | Glu | Leu | Arg | Ser | Leu | Arg | Ser | Asp | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Gly | Tyr | Arg | Trp | Phe | Ala | Tyr | Trp | Gly | Gln | Gly | Thr | Leu | Val |
|---|---|---|---|---|---|---|---|---|---|---|---|---|---|---|---|
| | | | 100 | | | | | 105 | | | | | 110 | | |

| Thr | Val | Ser | Ser |
|---|---|---|---|
| | | | 115 |

<210> SEQ ID NO 98
<211> LENGTH: 116
<212> TYPE: PRT
<213> ORGANISM: Artificial
<220> FEATURE:
<223> OTHER INFORMATION: Synthetic construct

<400> SEQUENCE: 98

| Gln | Val | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Thr | Phe | Thr | Asp | Tyr |
|---|---|---|---|---|---|---|---|---|---|---|---|---|---|---|---|
| | | | 20 | | | | | 25 | | | | | 30 | | |

| Asn | Met | His | Trp | Val | Arg | Gln | Ala | Pro | Gly | Gln | Gly | Leu | Glu | Trp | Met |
|---|---|---|---|---|---|---|---|---|---|---|---|---|---|---|---|
| | | 35 | | | | | 40 | | | | | 45 | | | |

| Gly | Gln | Ile | Tyr | Pro | Tyr | Asp | Gly | Asp | Thr | Gly | Tyr | Asn | Gln | Lys | Phe |
|---|---|---|---|---|---|---|---|---|---|---|---|---|---|---|---|
| | 50 | | | | | 55 | | | | | 60 | | | | |

| Lys | Ser | Arg | Val | Thr | Met | Thr | Thr | Asp | Thr | Ser | Thr | Ser | Thr | Ala | Tyr |
|---|---|---|---|---|---|---|---|---|---|---|---|---|---|---|---|
| 65 | | | | | 70 | | | | | 75 | | | | | 80 |

| Met | Glu | Leu | Arg | Ser | Leu | Arg | Ser | Asp | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Gly | Tyr | Arg | Trp | Phe | Ala | Tyr | Trp | Gly | Gln | Gly | Thr | Leu | Val |
|---|---|---|---|---|---|---|---|---|---|---|---|---|---|---|---|
| | | | 100 | | | | | 105 | | | | | 110 | | |

| Thr | Val | Ser | Ser |
|---|---|---|---|
| | | | 115 |

<210> SEQ ID NO 99
<211> LENGTH: 116
<212> TYPE: PRT
<213> ORGANISM: Artificial
<220> FEATURE:
<223> OTHER INFORMATION: Synthetic construct

<400> SEQUENCE: 99

| Gln | Val | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Thr | Phe | Phe | Asp | Tyr |
|---|---|---|---|---|---|---|---|---|---|---|---|---|---|---|---|
| | | | 20 | | | | | 25 | | | | | 30 | | |

| Asn | Met | His | Trp | Val | Arg | Gln | Ala | Pro | Gly | Gln | Gly | Leu | Glu | Trp | Met |

```
                35                  40                  45
Gly Tyr Ile Tyr Pro Tyr Asp Gly Asp Thr Gly Tyr Asn Gln Lys Phe
     50                  55                  60

Lys Ser Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Tyr Arg Trp Phe Ala Tyr Trp Gly Gln Gly Thr Leu Val
                100                 105                 110

Thr Val Ser Ser
            115

<210> SEQ ID NO 100
<211> LENGTH: 116
<212> TYPE: PRT
<213> ORGANISM: Artificial
<220> FEATURE:
<223> OTHER INFORMATION: Synthetic construct

<400> SEQUENCE: 100

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                 20                  25                  30

Asn Met His Trp Val Arg Gln Ala Pro Gly Gln Gly Leu Glu Trp Met
             35                  40                  45

Gly Tyr Ile Tyr Pro Tyr Asp Gly Asp Thr Gly Tyr Asn Gln Lys Phe
     50                  55                  60

Lys Ser Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Tyr Arg Trp Phe Ala Tyr Trp Gly Gln Gly Thr Leu Val
                100                 105                 110

Thr Val Ser Ser
            115

<210> SEQ ID NO 101
<211> LENGTH: 116
<212> TYPE: PRT
<213> ORGANISM: Artificial
<220> FEATURE:
<223> OTHER INFORMATION: Synthetic construct

<400> SEQUENCE: 101

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                 20                  25                  30

Asn Met His Trp Val Arg Gln Ala Pro Gly Gln Gly Leu Glu Trp Met
             35                  40                  45

Gly Tyr Ile Tyr Pro Tyr Asp Gly Asp Thr Gly His Asn Gln Lys Phe
     50                  55                  60

Lys Ser Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95
```

```
Ala Arg Gly Tyr Arg Trp Phe Ala Tyr Trp Gly Gln Gly Thr Leu Val
            100                 105                 110

Thr Val Ser Ser
        115

<210> SEQ ID NO 102
<211> LENGTH: 116
<212> TYPE: PRT
<213> ORGANISM: Artificial
<220> FEATURE:
<223> OTHER INFORMATION: Synthetic construct

<400> SEQUENCE: 102

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Asn Met His Trp Val Arg Gln Ala Pro Gly Gln Gly Leu Glu Trp Met
            35                  40                  45

Gly Tyr Ile Tyr Pro Tyr Asp Gly Asp Thr Gly Leu Asn Gln Lys Phe
        50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Arg Trp Phe Ala Tyr Trp Gly Gln Gly Thr Leu Val
            100                 105                 110

Thr Val Ser Ser
        115

<210> SEQ ID NO 103
<211> LENGTH: 116
<212> TYPE: PRT
<213> ORGANISM: Artificial
<220> FEATURE:
<223> OTHER INFORMATION: Synthetic construct

<400> SEQUENCE: 103

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Asn Met His Trp Val Arg Gln Ala Pro Gly Gln Gly Leu Glu Trp Met
            35                  40                  45

Gly Tyr Ile Tyr Pro Tyr Asp Gly Asp Thr Gly Tyr Asn Lys Lys Phe
        50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Arg Trp Phe Ala Tyr Trp Gly Gln Gly Thr Leu Val
            100                 105                 110

Thr Val Ser Ser
        115

<210> SEQ ID NO 104
<211> LENGTH: 116
<212> TYPE: PRT
<213> ORGANISM: Artificial
```

```
<220> FEATURE:
<223> OTHER INFORMATION: Synthetic construct

<400> SEQUENCE: 104

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Met
        35                  40                  45

Gly Tyr Ile Tyr Pro Tyr Asp Gly Asp Thr Gly Ile Asn Gln Lys Phe
    50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Arg Trp Phe Ala Tyr Trp Gly Gln Gly Thr Leu Val
            100                 105                 110

Thr Val Ser Ser
        115

<210> SEQ ID NO 105
<211> LENGTH: 116
<212> TYPE: PRT
<213> ORGANISM: Artificial
<220> FEATURE:
<223> OTHER INFORMATION: Synthetic construct

<400> SEQUENCE: 105

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Thr Asp Tyr
            20                  25                  30

Asn Met Val Trp Val Arg Gln Ala Pro Gly Gln Gly Leu Glu Trp Met
        35                  40                  45

Gly Tyr Ile Tyr Pro Tyr Asp Gly Glu Thr Gly Tyr Asn Gln Lys Phe
    50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Arg Ala Phe Glu Tyr Trp Gly Gln Gly Thr Leu Val
            100                 105                 110

Thr Val Ser Ser
        115

<210> SEQ ID NO 106
<211> LENGTH: 115
<212> TYPE: PRT
<213> ORGANISM: Artificial
<220> FEATURE:
<223> OTHER INFORMATION: Synthetic construct

<400> SEQUENCE: 106

Val Gln Leu Val Gln Ser Gly Ala Glu Val Lys Lys Pro Gly Ala Ser
1               5                   10                  15

Val Lys Val Ser Cys Lys Ala Ser Gly Tyr Asp Phe Thr Asp Tyr Asn
            20                  25                  30
```

Met Val Trp Val Arg Gln Ala Pro Gly Gln Gly Leu Glu Trp Met Gly
            35                  40                  45

Ser Ile Tyr Pro Tyr Asp Gly Glu Thr Gly Tyr Asn Pro Lys Phe Lys
    50                  55                  60

Ser Arg Val Thr Met Thr Thr Asp Thr Ser Thr Ser Thr Ala Tyr Met
65                  70                  75                  80

Glu Leu Arg Ser Leu Arg Ser Asp Asp Thr Ala Val Tyr Tyr Cys Ala
                85                  90                  95

Arg Gly Tyr Arg Ala Phe Glu Tyr Trp Gly Gln Gly Thr Leu Val Thr
            100                 105                 110

Val Ser Ser
        115

<210> SEQ ID NO 107
<211> LENGTH: 116
<212> TYPE: PRT
<213> ORGANISM: Artificial
<220> FEATURE:
<223> OTHER INFORMATION: Synthetic construct

<400> SEQUENCE: 107

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Thr Asp Tyr
            20                  25                  30

Asn Met Val Trp Val Arg Gln Ala Pro Gly Gln Gly Leu Glu Trp Met
            35                  40                  45

Gly Ser Ile Tyr Pro Tyr Asp Gly Glu Thr Gly Tyr Asn Gln Lys Phe
    50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Arg Ala Phe Glu Tyr Trp Gly Gln Gly Thr Leu Val
            100                 105                 110

Thr Val Ser Ser
        115

<210> SEQ ID NO 108
<211> LENGTH: 116
<212> TYPE: PRT
<213> ORGANISM: Artificial
<220> FEATURE:
<223> OTHER INFORMATION: Synthetic construct

<400> SEQUENCE: 108

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Glu Asp Tyr
            20                  25                  30

Asn Ile His Trp Val Arg Gln Ala Pro Gly Gln Gly Leu Glu Trp Met
            35                  40                  45

Gly Tyr Ile Tyr Pro Tyr Asp Gly Glu Thr Gly Tyr Asn Gln Lys Phe
    50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

```
Ala Arg Gly Tyr Arg Ala Phe Glu Tyr Trp Gly Gln Gly Thr Leu Val
                100                 105                 110

Thr Val Ser Ser
        115

<210> SEQ ID NO 109
<211> LENGTH: 116
<212> TYPE: PRT
<213> ORGANISM: Artificial
<220> FEATURE:
<223> OTHER INFORMATION: Synthetic construct

<400> SEQUENCE: 109

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Thr Asp Tyr
                20                  25                  30

Asn Met His Trp Val Arg Gln Ala Pro Gly Gln Gly Leu Glu Trp Met
            35                  40                  45

Gly Tyr Ile Tyr Pro Tyr Asp Gly Glu Thr Gly Tyr Asn Gln Lys Phe
    50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Arg Ala Phe Glu Tyr Trp Gly Gln Gly Thr Leu Val
                100                 105                 110

Thr Val Ser Ser
        115

<210> SEQ ID NO 110
<211> LENGTH: 116
<212> TYPE: PRT
<213> ORGANISM: Artificial
<220> FEATURE:
<223> OTHER INFORMATION: Synthetic construct

<400> SEQUENCE: 110

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Asn Ile His Trp Val Arg Gln Ala Pro Gly Gln Gly Leu Glu Trp Met
            35                  40                  45

Gly Tyr Ile Tyr Pro Tyr Asp Gly Glu Thr Gly Tyr Asn Gln Lys Phe
    50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Arg Ala Phe Glu Tyr Trp Gly Gln Gly Thr Leu Val
                100                 105                 110

Thr Val Ser Ser
        115

<210> SEQ ID NO 111
<211> LENGTH: 116
<212> TYPE: PRT
```

<213> ORGANISM: Artificial
<220> FEATURE:
<223> OTHER INFORMATION: Synthetic construct

<400> SEQUENCE: 111

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Asp Phe Glu Asp Tyr
            20                  25                  30
Asn Met His Trp Val Arg Gln Ala Pro Gly Gln Gly Leu Glu Trp Met
        35                  40                  45
Gly Tyr Ile Tyr Pro Tyr Asp Gly Glu Thr Gly Tyr Asn Pro Lys Phe
    50                  55                  60
Lys Ser Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Gly Tyr Arg Ala Phe Glu Tyr Trp Gly Gln Gly Thr Leu Val
            100                 105                 110
Thr Val Ser Ser
        115
```

<210> SEQ ID NO 112
<211> LENGTH: 116
<212> TYPE: PRT
<213> ORGANISM: Artificial
<220> FEATURE:
<223> OTHER INFORMATION: Synthetic construct

<400> SEQUENCE: 112

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
Asn Met His Trp Val Arg Gln Ala Pro Gly Gln Gly Leu Glu Trp Met
        35                  40                  45
Gly Tyr Ile Tyr Pro Tyr Asp Gly Asp Thr Gly Tyr Asn Gln Lys Phe
    50                  55                  60
Lys Ser Arg Val Thr Met Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Gly Tyr Arg Ala Phe Glu Tyr Trp Gly Gln Gly Thr Leu Val
            100                 105                 110
Thr Val Ser Ser
        115
```

<210> SEQ ID NO 113
<211> LENGTH: 116
<212> TYPE: PRT
<213> ORGANISM: Artificial
<220> FEATURE:
<223> OTHER INFORMATION: Synthetic construct

<400> SEQUENCE: 113

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
```

Asn Val His Trp Val Arg Gln Ala Pro Gly Gln Gly Leu Glu Trp Met
            35                  40                  45

Gly Tyr Ile Tyr Pro Tyr Asp Gly Asp Thr Gly Tyr Asn Gln Lys Phe
        50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Arg Ala Phe Glu Tyr Trp Gly Gln Gly Thr Leu Val
            100                 105                 110

Thr Val Ser Ser
        115

<210> SEQ ID NO 114
<211> LENGTH: 116
<212> TYPE: PRT
<213> ORGANISM: Artificial
<220> FEATURE:
<223> OTHER INFORMATION: Synthetic construct

<400> SEQUENCE: 114

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Ala Trp Val Arg Gln Ala Pro Gly Gln Gly Leu Glu Trp Met
            35                  40                  45

Gly Tyr Ile Tyr Pro Tyr Asp Gly Asp Thr Gly Tyr Asn Gln Lys Phe
        50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Arg Ala Phe Glu Tyr Trp Gly Gln Gly Thr Leu Val
            100                 105                 110

Thr Val Ser Ser
        115

<210> SEQ ID NO 115
<211> LENGTH: 116
<212> TYPE: PRT
<213> ORGANISM: Artificial
<220> FEATURE:
<223> OTHER INFORMATION: Synthetic construct

<400> SEQUENCE: 115

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Met
            35                  40                  45

Gly Tyr Ile Tyr Pro Tyr Asp Gly Asp Thr Gly Val Asn Gln Lys Phe
        50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys

```
                    85                  90                  95
Ala Arg Gly Tyr Arg Ala Phe Glu Tyr Trp Gly Gln Gly Thr Leu Val
                100                 105                 110
Thr Val Ser Ser
        115

<210> SEQ ID NO 116
<211> LENGTH: 116
<212> TYPE: PRT
<213> ORGANISM: Artificial
<220> FEATURE:
<223> OTHER INFORMATION: Synthetic construct

<400> SEQUENCE: 116

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Asn Ile His Trp Val Arg Gln Ala Pro Gly Gln Gly Leu Glu Trp Met
            35                  40                  45

Gly Tyr Ile Tyr Pro Tyr Asp Gly Glu Thr Gly Tyr Asn Gln Lys Phe
    50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Arg Trp Leu Glu Tyr Trp Gly Gln Gly Thr Leu Val
                100                 105                 110

Thr Val Ser Ser
        115

<210> SEQ ID NO 117
<211> LENGTH: 116
<212> TYPE: PRT
<213> ORGANISM: Artificial
<220> FEATURE:
<223> OTHER INFORMATION: Synthetic construct

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Asn Ile His Trp Val Arg Gln Ala Pro Gly Gln Gly Leu Glu Trp Met
            35                  40                  45

Gly Tyr Ile Tyr Pro Tyr Asp Gly Glu Thr Gly Tyr Asn Gln Lys Phe
    50                  55                  60

Lys Ser Arg Val Thr Met Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Arg Trp Phe Ala Tyr Trp Gly Gln Gly Thr Leu Val
                100                 105                 110

Thr Val Ser Ser
        115

<210> SEQ ID NO 118
<211> LENGTH: 116
```

```
<212> TYPE: PRT
<213> ORGANISM: Artificial
<220> FEATURE:
<223> OTHER INFORMATION: Synthetic construct

<400> SEQUENCE: 118

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Met
        35                  40                  45

Gly Tyr Ile Tyr Pro Tyr Asp Gly Glu Thr Gly Tyr Asn Gln Lys Phe
    50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Arg Trp Leu Ala Tyr Trp Gly Gln Gly Thr Leu Val
            100                 105                 110

Thr Val Ser Ser
        115

<210> SEQ ID NO 119
<211> LENGTH: 116
<212> TYPE: PRT
<213> ORGANISM: Artificial
<220> FEATURE:
<223> OTHER INFORMATION: Synthetic construct

<400> SEQUENCE: 119

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Ile His Trp Val Arg Gln Ala Pro Gly Gln Gly Leu Glu Trp Met
        35                  40                  45

Gly Tyr Ile Tyr Pro Tyr Asp Gly Glu Thr Gly Tyr Asn Gln Lys Phe
    50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Arg Trp Leu Ala Tyr Trp Gly Gln Gly Thr Leu Val
            100                 105                 110

Thr Val Ser Ser
        115

<210> SEQ ID NO 120
<211> LENGTH: 116
<212> TYPE: PRT
<213> ORGANISM: Artificial
<220> FEATURE:
<223> OTHER INFORMATION: Synthetic construct

<400> SEQUENCE: 120

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
```

```
                    20                  25                  30
Asn Met His Trp Val Arg Gln Ala Pro Gly Gln Gly Leu Glu Trp Met
        35                  40                  45

Gly Tyr Ile Tyr Pro Tyr Asp Gly Asp Thr Gly Tyr Asn Ser Lys Phe
 50                  55                  60

Lys Ser Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Tyr Arg Trp Phe Ala Tyr Trp Gly Gln Gly Thr Leu Val
                100                 105                 110

Thr Val Ser Ser
        115

<210> SEQ ID NO 121
<211> LENGTH: 116
<212> TYPE: PRT
<213> ORGANISM: Artificial
<220> FEATURE:
<223> OTHER INFORMATION: Synthetic construct

<400> SEQUENCE: 121

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                20                  25                  30

Asn Met His Trp Val Arg Gln Ala Pro Gly Gln Gly Leu Glu Trp Met
        35                  40                  45

Gly Tyr Ile Tyr Pro Tyr Asp Gly Asp Thr Gly Tyr Asn Gln Lys Tyr
 50                  55                  60

Lys Ser Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Tyr Arg Trp Phe Ala Tyr Trp Gly Gln Gly Thr Leu Val
                100                 105                 110

Thr Val Ser Ser
        115

<210> SEQ ID NO 122
<211> LENGTH: 116
<212> TYPE: PRT
<213> ORGANISM: Artificial
<220> FEATURE:
<223> OTHER INFORMATION: Synthetic construct

<400> SEQUENCE: 122

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
                20                  25                  30

Asn Met His Trp Val Arg Gln Ala Pro Gly Gln Gly Leu Glu Trp Met
        35                  40                  45

Gly Tyr Ile Tyr Pro Tyr Asp Gly Asp Thr Gly Ser Asn Gln Lys Phe
 50                  55                  60

Lys Ser Arg Val Thr Met Thr Thr Asp Thr Ser Thr Ser Thr Ala Tyr
 65                  70                  75                  80
```

```
Met Glu Leu Arg Ser Leu Arg Ser Asp Asp Thr Ala Val Tyr Tyr Cys
                85                  90                  95

Ala Arg Gly Tyr Arg Trp Phe Ala Tyr Trp Gly Gln Gly Thr Leu Val
            100                 105                 110

Thr Val Ser Ser
        115

<210> SEQ ID NO 123
<211> LENGTH: 116
<212> TYPE: PRT
<213> ORGANISM: Artificial
<220> FEATURE:
<223> OTHER INFORMATION: Synthetic construct

<400> SEQUENCE: 123

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Glu Asp Tyr
            20                  25                  30

Asn Met His Trp Val Arg Gln Ala Pro Gly Gln Gly Leu Glu Trp Met
        35                  40                  45

Gly Tyr Ile Tyr Pro Tyr Asp Gly Glu Thr Gly Tyr Asn Gln Lys Phe
    50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Arg Trp Leu Ala Tyr Trp Gly Gln Gly Thr Leu Val
            100                 105                 110

Thr Val Ser Ser
        115

<210> SEQ ID NO 124
<211> LENGTH: 116
<212> TYPE: PRT
<213> ORGANISM: Artificial
<220> FEATURE:
<223> OTHER INFORMATION: Synthetic construct

<400> SEQUENCE: 124

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Glu Asp Tyr
            20                  25                  30

Asn Met His Trp Val Arg Gln Ala Pro Gly Gln Gly Leu Glu Trp Met
        35                  40                  45

Gly Tyr Ile Tyr Pro Tyr Asp Gly Glu Thr Gly Tyr Asn Gln Lys Phe
    50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Arg Trp Phe Ala Tyr Trp Gly Gln Gly Thr Leu Val
            100                 105                 110

Thr Val Ser Ser
        115

<210> SEQ ID NO 125
```

```
<211> LENGTH: 116
<212> TYPE: PRT
<213> ORGANISM: Artificial
<220> FEATURE:
<223> OTHER INFORMATION: Synthetic construct

<400> SEQUENCE: 125

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Asn Ile His Trp Val Arg Gln Ala Pro Gly Gln Gly Leu Glu Trp Met
            35                  40                  45

Gly Tyr Ile Tyr Pro Tyr Asp Gly Glu Thr Gly Tyr Asn Pro Lys Phe
        50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Arg Trp Phe Ala Tyr Trp Gly Gln Gly Thr Leu Val
            100                 105                 110

Thr Val Ser Ser
        115

<210> SEQ ID NO 126
<211> LENGTH: 9
<212> TYPE: PRT
<213> ORGANISM: Unknown
<220> FEATURE:
<223> OTHER INFORMATION: Synthetic construct

<400> SEQUENCE: 126

Gln Gln Trp Asp Leu Asn Pro Pro Ala
1               5

<210> SEQ ID NO 127
<211> LENGTH: 9
<212> TYPE: PRT
<213> ORGANISM: Unknown
<220> FEATURE:
<223> OTHER INFORMATION: Synthetic construct

<400> SEQUENCE: 127

Gln Gln Trp Asp Ser Asn Pro Pro Ala
1               5

<210> SEQ ID NO 128
<211> LENGTH: 17
<212> TYPE: PRT
<213> ORGANISM: Unknown
<220> FEATURE:
<223> OTHER INFORMATION: Synthetic construct

<400> SEQUENCE: 128

Tyr Ile Tyr Pro Tyr Asn Gly Asp Thr Gly Tyr Asn Gln Lys Phe Lys
1               5                   10                  15

Ser

<210> SEQ ID NO 129
<211> LENGTH: 10
<212> TYPE: PRT
<213> ORGANISM: Unknown
<220> FEATURE:
```

-continued

<223> OTHER INFORMATION: Synthetic construct

<400> SEQUENCE: 129

Gly Tyr Thr Phe Thr Asp Tyr Thr Met His
1               5                   10

<210> SEQ ID NO 130
<211> LENGTH: 213
<212> TYPE: PRT
<213> ORGANISM: Artificial
<220> FEATURE:
<223> OTHER INFORMATION: Synthetic construct

<400> SEQUENCE: 130

Asp Ile Gln Met Thr Gln Ser Pro Ser Leu Ser Ala Ser Val Gly
1               5                   10                  15

Asp Arg Val Thr Ile Thr Cys Glu Ala Ser Ser Val Ser Tyr Met
                20                  25                  30

His Trp Tyr Gln Gln Lys Pro Gly Lys Ala Pro Lys Pro Leu Ile Tyr
                35                  40                  45

Ala Thr Ser Asn Leu Ala Ser Gly Val Pro Ser Arg Phe Ser Gly Ser
            50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 131
<211> LENGTH: 442
<212> TYPE: PRT
<213> ORGANISM: Artificial
<220> FEATURE:
<223> OTHER INFORMATION: Synthetic construct

<400> SEQUENCE: 131

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Asn Met His Trp Val Arg Gln Ala Pro Gly Gln Gly Leu Glu Trp Met
                35                  40                  45

Gly Tyr Ile Tyr Pro Tyr Asp Gly Asp Thr Gly Tyr Asn Gln Lys Phe

```
                50                  55                  60
Lys Ser Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                     85                  90                  95

Ala Arg Gly Tyr Arg Trp Phe Ala Tyr Trp Gly Gln Gly Thr Leu Val
                    100                 105                 110

Thr Val Ser Ser Ala Ser Thr Lys Gly Pro Ser Val Phe Pro Leu Ala
                115                 120                 125

Pro Cys Ser Arg Ser Thr Ser Glu Ser Thr Ala Ala Leu Gly Cys Leu
            130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Pro
210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
                260                 265                 270

Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
                340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
                420                 425                 430

Thr Gln Lys Ser Leu Ser Leu Ser Leu Gly
            435                 440

<210> SEQ ID NO 132
<211> LENGTH: 213
<212> TYPE: PRT
<213> ORGANISM: Artificial
```

```
<220> FEATURE:
<223> OTHER INFORMATION: Synthetic construct

<400> SEQUENCE: 132

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Pro Tyr Met
            20                  25                  30

His Trp Phe Gln Gln Lys Pro Gly Lys Ala Pro Lys Ser Leu Ile Tyr
        35                  40                  45

Ala Thr Ser Asn Pro Ala Tyr Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
        210

<210> SEQ ID NO 133
<211> LENGTH: 442
<212> TYPE: PRT
<213> ORGANISM: Artificial
<220> FEATURE:
<223> OTHER INFORMATION: Synthetic construct

<400> SEQUENCE: 133

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Ile His Trp Val Arg Gln Ala Pro Gly Gln Gly Leu Glu Trp Met
        35                  40                  45

Gly Tyr Ile Tyr Pro Tyr Asp Gly Glu Thr Gly Tyr Asn Gln Lys Phe
    50                  55                  60

Lys Ser Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Arg Trp Phe Ala Tyr Trp Gly Gln Gly Thr Leu Val
            100                 105                 110

Thr Val Ser Ser Ala Ser Thr Lys Gly Pro Ser Val Phe Pro Leu Ala
```

```
            115                 120                 125
Pro Cys Ser Arg Ser Thr Ser Glu Ser Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
210                 215                 220

Cys Pro Ala Pro Glu Phe Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
        370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly
        435                 440

<210> SEQ ID NO 134
<211> LENGTH: 442
<212> TYPE: PRT
<213> ORGANISM: Artificial
<220> FEATURE:
<223> OTHER INFORMATION: Synthetic construct

<400> SEQUENCE: 134

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asp Phe Thr Asp Tyr
                20                  25                  30

Asn Ile His Trp Val Arg Gln Ala Pro Gly Gln Gly Leu Glu Trp Met
```

-continued

```
                35                  40                  45
Gly Tyr Ile Tyr Pro Tyr Asp Gly Glu Thr Gly Tyr Asn Gln Lys Phe
 50                  55                  60
Lys Ser Arg Val Thr Met Thr Thr Asp Thr Ser Thr Ser Thr Ala Tyr
 65                  70                  75                  80
Met Glu Leu Arg Ser Leu Arg Ser Asp Asp Thr Ala Val Tyr Tyr Cys
                 85                  90                  95
Ala Arg Gly Tyr Arg Trp Leu Ala Tyr Trp Gly Gln Gly Thr Leu Val
                100                 105                 110
Thr Val Ser Ser Ala Ser Thr Lys Gly Pro Ser Val Phe Pro Leu Ala
            115                 120                 125
Pro Cys Ser Arg Ser Thr Ser Glu Ser Thr Ala Ala Leu Gly Cys Leu
130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Lys Thr Tyr Thr Cys Asn Val Asp His Lys Pro Ser Asn Thr
            195                 200                 205
Lys Val Asp Lys Arg Val Glu Ser Lys Tyr Gly Pro Pro Cys Pro Pro
210                 215                 220
Cys Pro Ala Pro Glu Phe Leu Gly Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser Gln Glu Asp Pro Glu Val Gln Phe Asn
            260                 265                 270
Trp Tyr Val Asp Gly Val Glu Val His Asn Ala Lys Thr Lys Pro Arg
            275                 280                 285
Glu Glu Gln Phe Asn Ser Thr Tyr Arg Val Val Ser Val Leu Thr Val
290                 295                 300
Leu His Gln Asp Trp Leu Asn Gly Lys Glu Tyr Lys Cys Lys Val Ser
305                 310                 315                 320
Asn Lys Gly Leu Pro Ser Ser Ile Glu Lys Thr Ile Ser Lys Ala Lys
                325                 330                 335
Gly Gln Pro Arg Glu Pro Gln Val Tyr Thr Leu Pro Pro Ser Gln Glu
            340                 345                 350
Glu Met Thr Lys Asn Gln Val Ser Leu Thr Cys Leu Val Lys Gly Phe
            355                 360                 365
Tyr Pro Ser Asp Ile Ala Val Glu Trp Glu Ser Asn Gly Gln Pro Glu
            370                 375                 380
Asn Asn Tyr Lys Thr Thr Pro Pro Val Leu Asp Ser Asp Gly Ser Phe
385                 390                 395                 400
Phe Leu Tyr Ser Arg Leu Thr Val Asp Lys Ser Arg Trp Gln Glu Gly
                405                 410                 415
Asn Val Phe Ser Cys Ser Val Met His Glu Ala Leu His Asn His Tyr
            420                 425                 430
Thr Gln Lys Ser Leu Ser Leu Ser Leu Gly
            435                 440

<210> SEQ ID NO 135
```

```
<211> LENGTH: 213
<212> TYPE: PRT
<213> ORGANISM: Artificial
<220> FEATURE:
<223> OTHER INFORMATION: Synthetic construct

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Val Ser Tyr Met
            20                  25                  30

His Trp Tyr Gln Gln Lys Pro Gly Lys Ala Pro Lys Pro Leu Ile Tyr
        35                  40                  45

Ala Thr Ser Asn Leu Ala Tyr Gly Val Pro Ser Arg Phe Ser Gly Ser
    50                  55                  60

Gly Ser Gly Thr Asp Phe Thr Leu Thr Ile Ser Ser Leu Gln Pro Glu
65              70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 136
<211> LENGTH: 6
<212> TYPE: PRT
<213> ORGANISM: Homo sapiens

<400> SEQUENCE: 136

Tyr Tyr Val Gly Arg Lys
1               5

<210> SEQ ID NO 137
<211> LENGTH: 5
<212> TYPE: PRT
<213> ORGANISM: Homo sapiens

<400> SEQUENCE: 137

Tyr Val Gly Arg Lys
1               5

<210> SEQ ID NO 138
<211> LENGTH: 10
<212> TYPE: PRT
<213> ORGANISM: Artificial
<220> FEATURE:
<223> OTHER INFORMATION: Synthetic construct
```

```
<400> SEQUENCE: 138

Glu Ala Ser Ser Ser Val Ser Tyr Met His
1               5                   10

<210> SEQ ID NO 139
<211> LENGTH: 7
<212> TYPE: PRT
<213> ORGANISM: Artificial
<220> FEATURE:
<223> OTHER INFORMATION: Synthetic construct

<400> SEQUENCE: 139

Ala Thr Ser Asn Leu Ala Ser
1               5

<210> SEQ ID NO 140
<211> LENGTH: 9
<212> TYPE: PRT
<213> ORGANISM: Artificial
<220> FEATURE:
<223> OTHER INFORMATION: Synthetic construct

<400> SEQUENCE: 140

Gln Gln Trp Asp Leu Asn Pro Pro Ala
1               5

<210> SEQ ID NO 141
<211> LENGTH: 10
<212> TYPE: PRT
<213> ORGANISM: Artificial
<220> FEATURE:
<223> OTHER INFORMATION: Synthetic construct

<400> SEQUENCE: 141

Gly Tyr Thr Phe Thr Asp Tyr Asn Met His
1               5                   10

<210> SEQ ID NO 142
<211> LENGTH: 27
<212> TYPE: PRT
<213> ORGANISM: Artificial
<220> FEATURE:
<223> OTHER INFORMATION: Synthetic construct

<400> SEQUENCE: 142

Tyr Ile Tyr Pro Tyr Asp Gly Asp Thr Gly Tyr Asn Gln Lys Phe Lys
1               5                   10                  15

Ser Gly Tyr Thr Phe Thr Asp Tyr Asn Met His
            20                  25

<210> SEQ ID NO 143
<211> LENGTH: 7
<212> TYPE: PRT
<213> ORGANISM: Artificial
<220> FEATURE:
<223> OTHER INFORMATION: Synthetic construct

<400> SEQUENCE: 143

Gly Tyr Arg Trp Phe Ala Tyr
1               5

<210> SEQ ID NO 144
<211> LENGTH: 112
<212> TYPE: PRT
<213> ORGANISM: Artificial
```

<220> FEATURE:
<223> OTHER INFORMATION: Synthetic construct

<400> SEQUENCE: 144

Ala Leu Asp Thr Asn Tyr Cys Phe Ser Ser Thr Glu Lys Asn Cys Cys
1               5                   10                  15

Val Arg Gln Leu Tyr Ile Asp Phe Lys Arg Asp Leu Gly Trp Lys Trp
            20                  25                  30

Val His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Thr Ile Leu Tyr Tyr Val Gly Arg Thr Pro
                85                  90                  95

Lys Val Glu Gln Leu Ser Asn Met Ile Val Arg Ser Cys Lys Cys Ser
            100                 105                 110

<210> SEQ ID NO 145
<211> LENGTH: 4
<212> TYPE: PRT
<213> ORGANISM: Homo sapiens

<400> SEQUENCE: 145

Tyr Ser Lys Val
1

<210> SEQ ID NO 146
<211> LENGTH: 106
<212> TYPE: PRT
<213> ORGANISM: Artificial
<220> FEATURE:
<223> OTHER INFORMATION: SYNTHETIC CONSTRUCT

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Arg Ala Ser Ser Ser Val Pro Tyr Met
            20                  25                  30

His Trp Phe Gln Gln Lys Pro Gly Lys Ala Pro Lys Ser Leu Ile Tyr
        35                  40                  45

Ala Thr Ser Asn Pro Ala Tyr Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Asp Leu Asn Pro Pro Ala
                85                  90                  95

Phe Gly Gln Gly Thr Lys Leu Glu Ile Lys
            100                 105

<210> SEQ ID NO 147
<211> LENGTH: 1326
<212> TYPE: DNA
<213> ORGANISM: Artificial
<220> FEATURE:
<223> OTHER INFORMATION: SYNTHETIC CONSTRUCT

<400> SEQUENCE: 147
caggttcagc tggtgcagtc tggtgctgag gtgaagaagc ctggtgcctc agtgaaggtc      60

```
tcctgcaagg cttctggtta cgactttacc gactataaca tccactgggt gcgtcaggcc      120
cctggtcaag gtcttgagtg gatgggttat atctatcctt acgatggtga gacaggctat      180
aaccagaagt tcaagagccg tgtcaccatg accacagaca catccacgag cacagcctac      240
atggagctgc gtagcctgcg ttctgacgac acggccgtgt attactgtgc gcgtggctac      300
cgttggcttg cctactgggg ccagggcacc ctggtcaccg tctcctccgc tccaccaag       360 ggcccatcgg tcttcccgct agcgccctgc tccaggagca cctccgagag cacagccgcc      420
ctgggctgcc tggtcaagga ctacttcccc gaaccggtga cggtgtcgtg gaactcaggc      480
gccctgacca gcggcgtgca caccttcccg gctgtcctac agtcctcagg actctactcc      540
ctcagcagcg tggtgaccgt gccctccagc agcttgggca cgaagaccta cacctgcaac      600
gtagatcaca agcccagcaa caccaaggtg gacaagagag ttgagtccaa atatggtccc      660
ccatgcccac cctgcccagc acctgagttc ctggggggac catcagtctt cctgttcccc      720
ccaaaaccca aggacactct catgatctcc cggacccctg aggtcacgtg cgtggtggtg      780
gacgtgagcc aggaagaccc cgaggtccag ttcaactggt acgtggatgg cgtggaggtg      840
cataatgcca agacaaagcc gcgggaggag cagttcaaca gcacgtaccg tgtggtcagc      900
gtcctcaccg tcctgcacca ggactggctg aacggcaagg agtacaagtg caaggtctcc      960
aacaaaggcc tcccgtcctc catcgagaaa accatctcca agccaaagg gcagccccga     1020 gagccacagg tgtacaccct gcccccatcc caggaggaga tgaccaagaa ccaggtcagc     1080
ctgacctgcc tggtcaaagg cttctacccc agcgacatcg ccgtggagtg ggagagcaat     1140
gggcagccgg agaacaacta caagaccacg cctcccgtgc tggactccga cggctccttc     1200
ttcctctaca gcaggctaac cgtggacaag agcaggtggc aggagggaa tgtcttctca     1260 tgctccgtga tgcatgaggc tctgcacaac cactacacac agaagagcct ctccctgtct     1320
ctgggt                                                                1326

<210> SEQ ID NO 148
<211> LENGTH: 639
<212> TYPE: DNA
<213> ORGANISM: Artificial
<220> FEATURE:
<223> OTHER INFORMATION: SYNTHETIC CONSTRUCT

<400> SEQUENCE: 148
gacatccaga tgacccagtc tccatcctcc ctgtctgcat ctgtaggaga cagagtcacc       60
atcacttgcc gggcaagttc cagcgtgagc tatatgcact ggtatcagca gaaaccaggg      120
aaagccccta gccgctgat ctatgctacc tccaacttgg cctatggagt cccatcaagg       180
ttcagtggca gtggatctgg gacagatttc actctcacca tcagcagtct gcaacctgaa      240
gattttgcaa cttactactg tcagcagtgg gacctgaacc ctccagcctt cggccagggg      300
accaagctgg agatcaaacg aactgtggct gcaccatctg tcttcatctt cccgccatct      360
gatgagcagt tgaaatctgg aactgcctct gttgtgtgcc tgctgaataa cttctatccc      420
agagaggcca aagtacagtg gaaggtggat aacgccctcc aatcgggtaa ctcccaggag      480
agtgtcacag agcaggacag caaggacagc acctacagcc tcagcagcac cctgacgctg      540
agcaaagcag actacgagaa acacaaagtc tacgcctgcg aagtcaccca tcagggcctg      600
agctcgcccg tcacaaagag cttcaacagg ggagagtgc                              639

<210> SEQ ID NO 149
```

```
<211> LENGTH: 1326
<212> TYPE: DNA
<213> ORGANISM: Artificial
<220> FEATURE:
<223> OTHER INFORMATION: SYNTHETIC CONSTRUCT

<400> SEQUENCE: 149
caggttcagc tggtgcagtc tggtgctgag gtgaagaagc ctggtgcctc agtgaaggtc      60
tcctgcaagg cttctggtta caccttacc gactataaca tccactgggt gcgtcaggcc     120
cctggtcaag gtcttgagtg gatgggttat atctatcctt acgatggtga gacaggctat     180
aaccagaagt tcaagagccg tgtcaccatg accacagaca tccacgag cacagcctac       240
atggagctgc gtagcctgcg ttctgacgac acggccgtgt attactgtgc gcgtggctac     300
cgttggtttg cctactgggg ccagggcacc ctggtcaccg tctcctccgc ctccaccaag     360
ggcccatcgg tcttcccgct agcgccctgc tccaggagca cctccgagag cacagccgcc     420
ctgggctgcc tggtcaagga ctacttcccc gaaccggtga cggtgtcgtg gaactcaggc     480
gccctgacca gcggcgtgca ccttcccg gctgtcctac agtcctcagg actctactcc       540
ctcagcagcg tggtgaccgt gccctccagc agcttgggca cgaagaccta cacctgcaac     600
gtagatcaca agcccagcaa caccaaggtg gacaagagag ttgagtccaa atatggtccc     660
ccatgcccac cctgcccagc acctgagttc ctggggggac catcagtctt cctgttcccc     720
ccaaaaccca aggacactct catgatctcc cggacccctg aggtcacgtg cgtggtggtg     780
gacgtgagcc aggaagaccc cgaggtccag ttcaactggt acgtggatgg cgtggaggtg     840
cataatgcca agacaaagcc gcgggaggag cagttcaaca gcacgtaccg tgtggtcagc     900
gtcctcaccg tcctgcacca ggactggctg aacggcaagg agtacaagtg caaggtctcc     960
aacaaaggcc tcccgtcctc catcgagaaa accatctcca agccaaagg gcagccccga     1020
gagccacagg tgtacaccct gcccccatcc caggaggaga tgaccaagaa ccaggtcagc     1080
ctgacctgcc tggtcaaagg cttctacccc agcgacatcg ccgtggagtg ggagagcaat     1140
gggcagccgg agaacaacta caagaccacg cctcccgtgc tggactccga cggctccttc     1200
ttcctctaca gcaggctaac cgtggacaag agcaggtggc aggaggggaa tgtcttctca     1260
tgctccgtga tgcatgaggc tctgcacaac cactacacac agaagagcct ctccctgtct     1320
ctgggt                                                                1326

<210> SEQ ID NO 150
<211> LENGTH: 639
<212> TYPE: DNA
<213> ORGANISM: Artificial
<220> FEATURE:
<223> OTHER INFORMATION: SYNTHETIC CONSTRUCT

<400> SEQUENCE: 150
gacatccaga tgacccagtc tccatcctcc ctgtctgcat ctgtaggaga cagagtcacc      60
atcacttgcc gggcaagttc tagcgtgccc tatatgcact ggtttcagca gaaaccaggg     120
aaagccccta gtccttgat ctatgctacc tccaacccgg cctatggagt cccatcaagg      180
ttcagtggca gtggatctgg gacagatttc actctcacca tcagcagtct gcaacctgaa     240
gattttgcaa cttactactg tcagcagtgg gacctgaacc ctccagcctt cggccagggg     300
accaagctgg agatcaaacg aactgtggct gcaccatctg tcttcatctt cccgccatct     360
gatgagcagt tgaaatctgg aactgcctct gttgtgtgcc tgctgaataa cttctatccc     420
agagaggcca aagtacagtg gaaggtggat aacgccctcc aatcgggtaa ctcccaggag     480
```

-continued

```
agtgtcacag agcaggacag caaggacagc acctacagcc tcagcagcac cctgacgctg      540
agcaaagcag actacgagaa acacaaagtc tacgcctgcg aagtcaccca tcagggcctg      600
agctcgcccg tcacaaagag cttcaacagg ggagagtgc                             639
```

US 7,619,069 B2

ANTIBODIES TO TGF-BETA 1

Figure 1:
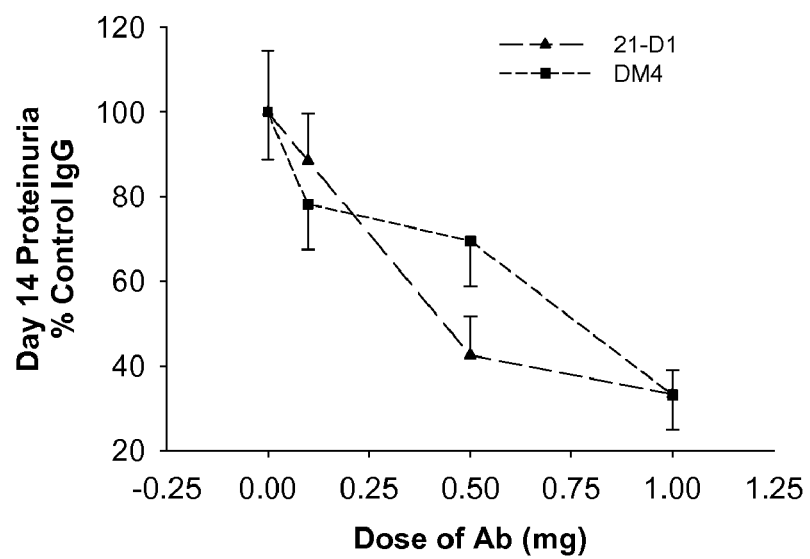

This application is a continuation-in-part of PCT International Application No. PCT/US2006/014943, filed Apr. 20, 2006, which claims the benefit of U.S. Provisional Application No. 60/674,082, filed Apr. 22, 2005.

The present invention is in the field of medicine, particularly in the field of antibodies that bind human TGF-beta 1 protein, and therapeutic use of the antibodies for treating various disorders or conditions in a human subject.

Members of the TGF-beta family control many cellular functions, and their activity is critical for regulating numerous developmental and homeostatic processes. One member of this family, TGF-beta 1, is involved in a variety of cellular processes, for example, cell proliferation and differentiation, migration, apoptosis, embryonic development, extracellular matrix formation, bone development, wound healing, hematopoiesis, and immune and inflammatory responses.

Additionally, preclinical and clinical data indicate that TGF-beta 1 is a major contributor to matrix protein deposition in interstitial fibrosis, and is involved in the initiation and progression of a number of associated fibrotic diseases, including renal fibrosis, which is common to all forms of chronic renal diseases (CRD). The extent of renal fibrosis positively correlates with progression to chronic renal failure (CRF), and can result in death, chronic dialysis, or renal transplantation.

TGF-beta is associated with CRF through complex and diverse events that impact the majority of cells of the kidney. These events ultimately result in both tubulointerstitial fibrosis and glomerulosclerosis leading to loss of nephron function and ultimately chronic renal failure. Of the three TGF-beta isoforms, TGF-beta 1 appears to predominate in mediating the progression of chronic renal disease, not only as being the most predominantly expressed isoform, but also as both TGF-beta 2 and -beta 3 appear to mediate their effects through up-regulation of TGF-beta 1 expression (Yu, 2003, Kid. Int. 64, 844). Consequently, to prevent the deleterious effects of disorders such as CRD, there is a need to modulate TGF beta 1 expression.

Anti-TGF beta 1 monoclonal antibodies (mAbs) are disclosed in WO 97/13844. The present invention provides new TGF-beta 1 specific antibodies with high binding affinity that are useful in the diagnosis, prevention, and treatment of fibrotic disorders such as chronic renal disease.

In a first aspect, the present invention provides an antibody or an antigen-binding fragment thereof, comprising a light chain variable region having the amino acid sequence shown in SEQ ID NO: 43 and a heavy chain variable region having the amino acid sequence shown in SEQ ID NO: 90, or a light chain variable region having the amino acid sequence shown in SEQ ID NO: 146 and a heavy chain variable region having the amino acid sequence shown in SEQ ID NO: 117.

In a preferred embodiment, antibodies of the invention comprises a light chain with the amino acid sequence shown in SEQ ID NO: 135 and a heavy chain with the amino acid sequence shown in SEQ ID NO: 134, or a light chain with the amino acid sequence shown in SEQ ID NO: 132 and a heavy chain with the amino acid sequence shown in SEQ ID NO: 133.

In another embodiment, the present invention also provides a pharmaceutical composition, comprising an antibody of the present invention and a pharmaceutically acceptable carrier, diluent, or excipient.

The antibody of the present invention can be present in an amount of from about 20 to about 100 mg/ml.

The pharmaceutical composition can comprise a surfactant, e.g., polyoxyethylene-sorbitan-20-monooleate (also known as polysorbate 80). Preferably, polysorbate 80 is present in an amount of from about 0.005% to about 0.05% by weight of the total composition.

In a preferred embodiment, the antibody is formulated in an aqueous composition with a pH-buffered solution. A citrate buffer, preferably 10 mM sodium citrate, at a pH range from about 5.5 to about 7.0, is preferred. More preferably, the pH is about 6.0 to about 6.5.

In another preferred embodiment, the pharmaceutical composition of the invention comprises about 50 to about 150 mM sodium chloride.

In another embodiment, the present invention also provides a method of treating a fibrotic disease, particularly a chronic renal disease, in a mammal, preferably a primate, and more preferably a human, comprising administering to a mammal in need of such treatment an effective amount of an antibody of the present invention.

In another embodiment, antibodies of the invention can be used in combination with a renal renin-angiotensin system (RAS) inhibitor for treating a chronic renal disease. The RAS inhibitor can be an angiotensin-converting enzyme (ACE) inhibitor, e.g., lisinopril or captopril, an angiotensin II receptor antagonist, e.g., losartan or irbesartan, or a combination of an ACE inhibitor and an angiotensin II receptor antagonist.

FIG. 1. shows the effects of antibodies of the invention on the urinary protein levels in rats. Rats are injected i.v. with 2.5 mg/kg of α.-Thy1.1 mAb followed 30 min later with 1 mg of Herceptin (control mAb), mAb21D1 and mAbDM4. A second dose of Herceptin, mAb21D1 and mAbDM4 is administered on day 7, and animals are euthanized on day 14. Both mAbs 21D1 and DM4 decrease urinary protein levels (proteinuria) in a dose dependent manner.

Antibody Characterization

The term "antibody" or "monoclonal antibody" refers to a composition with a homogeneous antibody population, comprising four polypeptide chains, two heavy chains and two light chains interconnected by disulfide bonds. Each heavy chain of a full-length antibody is comprised of an N-terminal heavy chain variable region (herein "HCVR") and a heavy chain constant region. Each light chain of a full-length antibody is comprised of an N-terminal light chain variable region (herein "LCVR") and a light chain constant region. The HCVR and LCVR regions can be further subdivided into regions of hypervariability, termed complementarity determining regions ("CDRs"), interspersed with regions that are more conserved, termed framework regions ("FRs"). The functional ability of an antibody to bind a particular antigen or epitope is largely influenced by the six CDRs present in the variable region of the antibody.

The term "antigen-binding fragment" refers to a portion or fragment of an intact antibody, comprising the antigen-binding or variable region thereof. Examples of antibody fragments include less than full length antibodies, e.g., a Fab fragment, F(ab')$_2$, or a single-chain variable fragment (scFv). Likewise encompassed by the invention are diabodies, linear antibodies, single-chain antibodies, fusion proteins, recombinant proteins, and multivalent or multispecific antibodies formed or partly formed from an antigen-binding fragment of the present invention.

A "binding site" is a specific region, area, or configuration of a molecular entity that takes part in the specific and/or selective binding with another molecular entity. A non-limiting example of a binding site is the contiguous amino acid sequence comprising a CDR of an antibody. In one embodiment, a binding site of the invention comprises a sequence having the formula shown in Tables 1a and 1b. In another non-limiting embodiment, a binding site comprises a combination of the sequences shown in these tables. Another non-limiting example is a binding site formed from the three-dimensional configuration and spatial organization of the amino acid sequences comprising the six CDR loops of the heavy and light variable chains at the rim of the eight-stranded beta barrel of a Fab fragment.

Specific binding of the present composition means that the binding composition has a binding site that recognizes a region of TGF-beta 1, typically in its native active conformation. For example, antibodies raised to a TGF-beta 1 and recognizing an epitope of TGF-beta 1 are capable of forming a binding composition:TGF-beta 1 complex by specific binding. An epitope of a binding composition of the invention can be determined using techniques described herein or in the art and/or as determined by competitive binding as described herein. In a preferred embodiment, an epitope of a binding composition of the invention comprises the amino acid residues YYVGRK [SEQ ID NO: 136] of SEQ ID NO: 1; in another embodiment, an epitope of a binding compositions of the invention comprises the amino acid residues YYVGRK [SEQ ID NO: 136] of SEQ ID NO: 1 and YSKV [SEQ ID NO: 145] of SEQ ID NO: 1; in an additional embodiment, an epitope of a binding composition of the invention comprises at least 1, 2, 3, 4, 5, or 6 residues (contiguous or non-contiguous) from YYVGRK [SEQ ID NO: 136] of SEQ ID NO: 1 and/or at least 1, 2, 3, or 4 residues (contiguous or non-contiguous) from YSKV [SEQ ID NO: 145] of SEQ ID NO: 1 (such an embodiment includes any and all combinations thereof such as, e.g. without limitation: YYVGRK [SEQ ID NO: 136] and KV of SEQ ID NO: 1; or YVGRK [SEQ ID NO: 137] and Y and KV of SEQ ID NO: 1 (all such combinations are available by using a computer algorithm and well known mathematical formulas for permutaions and combinations). In a still further preferred embodiment, an epitope of the invention is defined functionally, for example, by the ability of a binding composition of the invention to prevent formation of a subsequent binding complex by competing binding compositions for the same antigen such as, e.g., TGF-beta 1 (such competitive binding is described herein).

Applicants proviso out a binding composition which specifically and/or selectively binds TGF-beta 1 isoform over TGF-beta 2 and/or TGF-beta 3 and which neutralizes TGF-beta 1 comprising QQWDLNPPA [SEQ ID NO: 126]; QQWDSNPPA [SEQ ID NO: 127]; YIYPYNGDTGYNQK-FKS [SEQ ID NO: 128]; or GYTFTDYTMH [SEQ ID NO: 129].

Variable heavy and light chain CDRs of particular monoclonal antibody binding compositions of the invention are shown below in Tables 1a and 1b. The CDR regions are indicated using the standard amino acid single letter code and standard CDR numbering, (i.e., with the increasing numerical value of a CDR corresponding with its increasing proximity to the constant domain of a typical IgG heavy or light chain structure; e.g., VH CDR3 is more proximal to the CH1 domain than VH CDR1).

Specific CDR embodiments are represented generically using amino acid formulae to describe a genus of CDRs (again using standard single letter amino acid code with substitutable amino acid residues indicated by the letter "X" and their residue placement within a particular CDR indicated by a numeric subscript whose value increases from lowest (amino-most) to highest (carboxy-most) residue in the CDR (e.g., $X_1$ in VHCDR2 is the most amino residue of the CDR while the carboxy-most substitutable residue is $X_6$). Using these generic formulae, one of ordinary skill in the art can determine all CDR embodiments possible at each designated position in a variable heavy or light chain domain ($V_L$ or $V_H$) embodiment encompassed by the invention.

TABLE 1a

| CDR Heavy Chain Formula of Binding Compositions Heavy Chain CDRs | | |
|---|---|---|
| CDR1 | CDR2 | CDR3 |
| $GYX_1FX_2DYNX_3X_4$ * [SEQ ID NO: 2] | $X_1X_2YPYDGX_3TGX_4NX_5KX_6KS$ ** [SEQ ID NO: 3] | $GYRX_1X_2X_3Y$ *** [SEQ ID NO: 4] |

\* For VHCDR1: $X_1$ is either T or D; $X_2$ is either T, E, or F; $X_3$ is either M, I, L, or V; and $X_4$ is either H, V, or A.
\*\* For VHCDR2: $X_1$ is either Y, Q, or S; $X_2$ is either I, or V; $X_3$ is either D, or E; $X_4$ is either Y, T, H, or L; $X_5$ is either Q, K, P, or S; and $X_6$ is either F or Y.
\*\*\* For VHCDR3: $X_1$ is either W or A; $X_2$ is either F or L; and $X_3$ is either A, E, or Y.

TABLE 1b

| CDR Light Chain Formula of Binding Compositions Light Chain CDRs | | |
|---|---|---|
| CDR1 | CDR2 | CDR3 |
| $X_1AX_2X_3X_4VX_5YMH$ * [SEQ ID NO: 5] | $ATSNX_1AX_2$ ** [SEQ ID NO: 6] | $X_1QWDX_2X_3X_4PA$ *** [SEQ ID NO: 7] |

\* For VLCDR1: $X_1$ is either R, Y, E, or Q; $X_2$ is either S or T; $X_3$ is either S, V, or A; $X_4$ is either S or L; $X_5$ is either S, P, L, or Y.
\*\* For VLCDR2: $X_1$ is either L, N, or P; and $X_2$ is either S, K, Y, L, M, F, E, Q, R, or H.
\*\*\* For VLCDR3: $X_1$ is either Q or S; $X_2$ is either L, D, or P; $X_3$ is either N or R; and $X_4$ is either P, F, Y, or R.

Further, encompassed herein are antibody binding compositions using CDRs encompassed herein that are embedded (in appropriate orientation) or carried within human antibody framework regions to enable the resulting binding composition to specifically and/or selectively bind mature TGF-beta 1 over mature TGF-beta 2 and/or mature TGF-beta 3 and to neutralize mature TGF-beta 1. Art known techniques can be used to embed or place particular CDRs within appropriate frameworks. Variable domains employed in the invention may be derived from any germline or rearranged human variable domain, or may be a synthetic variable domain based on consensus sequences of known human variable domains.

Preferred variable domain frameworks are those that do not significantly affect the biological properties of an anti-TGF-beta 1 antibody binding composition, especially, the ability to specifically and/or selectively bind and neutralize mature TGF-beta 1 over mature TGF-beta 2 and/or TGF-beta 3. More preferable are frameworks that additionally do not elicit significant immunogenic reactions when administered to a human subject (e.g., parenterally). Preferred framework sequences can be sequences of naturally occurring human antibodies or consensus sequences of several human antibodies. Non-limiting examples of framework sequences for the heavy chain variable region of antibody embodiments of the invention include the VH segment DP-5 (Tomlinson, et al. 1992 *J. Mol. Biol.* 227:776-98) and the J segment JH4, JH1 or JH5 (Ravetch, et al. 1981 *Cell* 27:583-91). The Vk segment L1 (Cox, et al. 1994 *Eur. J. Immunol* 24:827-36) and the J segment Jk4 (Hieter, et al. 1982 *J. Biol. Chem.* 10:1516-22) are non-limiting example framework sequences for the light chain variable region. In a preferred embodiment, the HCVR FR1 framework comprises QVQLVQSGAEVKKPGAS-VKVSCKAS [SEQ ID NO: 8]; the HCVR FR2 framework comprises WVRQAPGQGLEWMG [SEQ ID NO: 9]; the HCVR FR3 framework comprises RVTMTTDTST-STAYMELRSLRSDDTAVYYCAR [SEQ ID NO: 10]; and the HCVR FR4 framework comprises WGQGTLVTVSS [SEQ ID NO: 11]. In another preferred embodiment, the LCVR FR1 framework comprises DIQMTQSPSSLSAS-VGDRVTITC [SEQ ID NO: 12]; the LCVR FR2 framework comprises a sequence selected from: [SEQ ID NO: 13-36], the LCVR FR3 framework comprises GVPSRFSGSGSGT-DFTLTISSLQPEDFATYYC [SEQ ID NO: 37]; and the LCVR FR4 framework comprises FGQGTKLEIK [SEQ ID NO: 38].

In one embodiment, a preferred heavy chain constant region for use in embedding antibody binding composition CDRs of the invention includes, for example, an IgG constant region. In a more preferred embodiment, the IgG constant region is an IgG1 constant region or an IgG4 constant region as shown below:

```
IgG1 [SEQ ID NO: 39]:
STKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPK

SCDKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCL

VKGFYPSDIAVEWESNGQPENNYKTTPPVLDSDGSFFLYSKLTVDKSRWQ

QGNVFSCSVMHEALHNHYTQKSLSLSPG;
or

IgG4 [SEQ ID NO: 40]
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLG
```

A preferred light chain constant region sequence of the invention is the kappa chain constant region shown below:

```
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC [SEQ ID NO: 41]
```

In another preferred embodiment, antibody binding compositions contain the IgG1 Heavy chain constant region or the IgG4 Heavy chain constant region and the kappa Light chain constant region.

Using the information provided herein, one of ordinary skill can create a mAb embodiment of the invention, for example, such as No. 46P-L 1-6, which would have a Light Chain comprising:

```
DIQMTQSPSSLSASVGDRVTITCEASSSVSYMHWYQQKPGKAPKPLIYAT

SNLASGVPSRFSGSGSGTDFTLTISSLQPEDFATYYCQQWDLNPPAFGQG

TKLEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC [SEQ ID NO: 130]
``` where:
the LCVR FR1 framework=DIQMTQSPSSLSAS VGDRVTITC[SEQ ID NO: 12];
the VL CDR1=EASSSVSYMH [SEQ ID NO: 138] of the formula $X_1AX_2X_3X_4VX_5YMH$ [SEQ ID NO: 5], where X1 is either R, Y, E, or Q; X2 is either S or T; X3 is either S, V, or A; X4 is either S or L; and X5 is either S, P, L, or Y;
the LCVR FR2 framework=WYQQKPGKAPKPLIY [SEQ ID NO: 13];
the VL CDR2=ATSNLAS [SEQ ID NO: 139] of the formula $ATSNX_1AX_2$ [SEQ ID NO: 6], where $X_1$ is either L, N, or P; and $X_2$ is either S, K, Y, L, M, F, E, Q, R, or H;
the LCVR FR3 framework=GVPSRFSGSGSGTDFTL TISSLQPEDFATYYC [SEQ ID NO: 37];
the VL CDR3=QQWDLNPPA [SEQ ID NO: 140] of the formula $X_1QWDX_2X_3X_4PA$ [SEQ ID NO: 7], where $X_1$ is either Q or S; $X_2$ is either L, D, or P; $X_3$ is either N or R; and $X_4$ is either P, F, Y, or R;
the LCVR FR4 framework=FGQGTKLEIK [SEQ ID NO: 38]; and
the Light Chain constant region=

```
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC; [SEQ ID NO: 41]
``` and a Heavy chain comprising:

```
QVQLVQSGAEVKKPGASVKVSCKASGYTFTDYNMHWVRQAPGQGLEWMGY

IYPYDGDTGYNQKFKSRVTMTTDTSTSTAYMELRSLRSDDTAVYYCARGY

RWFAYWGQGTLVTVSSASTKGPSVFPLAPCSRSTSESTAALGCLVKDYFP
```

-continued

EPVTVSWNSGALTSGVHTFPAVLQSSGLYSLSSVVTVPSSSLGTKTYTCN

VDHKPSNTKVDKRVESKYGPPCPPCPAPEFLGGPSVFLFPPKPKDTLMIS

RTPEVTCVVVDVSQEDPEVQFNWYVDGVEVHNAKTKPREEQFNSTYRVVS

VLTVLHQDWLNGKEYKCKVSNKGLPSSIEKTISKAKGQPREPQVYTLPPS

QEEMTKNQVSLTCLVKGFYPSDIAVEWESNGQPENNYKTTPPVLDSDGSF

FLYSRLTVDKSRWQEGNVFSCSVMHEALHNHYTQKSLSLSLG where: [SEQ ID NO: 131]

where:
the HCVR FR1 framework=QVQLVQSGAEVKK PGASVKVSCKAS [SEQ ID NO: 8];
the VH CDR1=GYTFTDYNMH [SEQ ID NO: 141] of the formula GYX$_1$FX$_2$DYNX$_3$X$_4$ GYTFTDYNMH [SEQ ID NO: 2]; X$_1$ is either T or D; X$_2$ is either T, E, or F; X$_3$ is either M, I, L, or V; and X$_4$ is either H, V, or A;
the HCVR FR2 framework=WVRQAPGQGLEWMG GYTFTDYNMH [SEQ ID NO: 9];
the VH CDR2=YIYPYDGDTGYNQKFKS GYTFT-DYNMH [SEQ ID NO: 142] of the formula X$_1$X$_2$YPYDGX$_3$TGX$_4$NX$_5$KX$_6$KS [SEQ ID NO: 3]; X$_1$ is either Y, Q, or S; X$_2$ is either I, or V; X$_3$ is either D, or E; X$_4$ is either Y, T, H, or L; X$_5$ is either Q, K, P, or S; and X$_6$ is either F or Y;
the HCVR FR3 framework=RVTMTTDTSTSTAYMEL RSLRSDDTAVYYCAR YIYPYDGDTGYNQKFKS GYTFTDYNMH [SEQ ID NO: 10];
the VH CDR3=GYRWFAY [SEQ ID NO: 143] of the formula GYRX$_1$X$_2$X$_3$Y [SEQ ID NO: 4]; where X$_1$ is either W or A; X$_2$ is either F or L; and X$_3$ is either A, E, or Y;
the HCVR FR4 framework=WGQGTLVTVSS [SEQ ID NO: 11]; and
the Heavy Chain constant region=

ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLG. [SEQ ID NO: 40]

The preferred antibodies of the invention are referred to herein as 21D1, DM4, DM7, C27, and 23A3. The amino acid sequences of variable regions of these antibodies are as follows:

A. Light Chain Variable Regions
21D1 (SEQ ID NO: 146)
DIQMTQSPSSLSASVGDRVTITCRASSSVPYMHWFQQKPGKAPKSLIYAT
SNPAYGVPSRFSGSGSGTDFTLTISSLQPEDFATYYCQQWDLNPPAFGQG
TKLEIK DM4 (SEQ ID NO: 43)
DIQMTQSPSSLSASVGDRVTITCRASSSVSYMHWYQQKPGKAPKPLIYAT
SNLAYGVPSRFSGSGSGTDFTLTISSLQPEDFATYYCQQWDLNPPAFGQG
TKLEIK DM7 (SEQ ID NO: 42)
DIQMTQSPSSLSASVGDRVTITCRASSSVSYMHWYQQKPGKAPKPLIYAT
SNLAKGVPSRFSGSGSGTDFTLTISSLQPEDFATYYCQQWDLNPPAFGQG
TKLEIK C27 (SEQ ID NO: 73)
DIQMTQSPSSLSASVGDRVTITCRASSSVPYMHWYQQKPEKAPKSLIYAT
SNLAFGVPSRFSGSGSGTDFTLTISSLQPEDFATYYCQQWDLNPPAFGQG
TKLEIK 23A3 (SEQ ID NO: 57)
DIQMTQSPSSLSASVGDRVTITCRASSSVPYMHWYQQKPGKAPKLLIYAT
SNPAYGVPSRFSGSGSGTDFTLTISSLQPEDFATYYCQQWDLNPPAFGQG
TKLEIK B. Heavy Chain Variable Regions
21D1 (SEQ ID NO: 117)
QVQLVQSGAEVKKPGASVKVSCKASGYTFTDYNIHWVRQAPGQGLEWMGY
IYPYDGETGYNQKFKSRVTMTTDTSTSTAYMELRSLRSDDTAVYYCARGY
RWFAYWGQGTLVTVSS DM4 (SEQ ID NO: 90)
QVQLVQSGAEVKKPGASVKVSCKASGYDFTDYNIHWVRQAPGQGLEWMGY
IYPYDGETGYNQKFKSRVTMTTDTSTSTAYMELRSLRSDDTAVYYCARGY
RWLAYWGQGTLVTVSS DM7 (SEQ ID NO: 92)
QVQLVQSGAEVKKPGASVKVSCKASGYDFTDYNMHWVRQAPGQGLEWMGY
IYPYDGETGYNQKFKSRVTMTTDTSTSTAYMELRSLRSDDTAVYYCARGY
RWLYYWGQGTLVTVSS C27 (SEQ ID NO: 119)
QVQLVQSGAEVKKPGASVKVSCKASGYTFTDYNIHWVRQAPGQGLEWMGY
IYPYDGETGYNQKFKSRVTMTTDTSTSTAYMELRSLRSDDTAVYYCARGY
RAFEYWGQGTLVTVSS 23A3 (SEQ ID NO: 107)
QVQLVQSGAEVKKPGASVKVSCKASGYDFTDYNMVWVRQAPGQGLEWMGS
IYPYDGETGYNQKFKSRVTMTTDTSTSTAYMELRSLRSDDTAVYYCARGY
RAFEYWGQGTLVTVSS Full-length antibodies of the invention are constructed by operably linking Fabs to an IgG$_4$ Fc region using standard techniques. For example, mAb 21D1 has a heavy chain with the amino acid sequence of SEQ ID NO: 133 encoded by the DNA sequence of SEQ ID NO: 149, and a light chain with the amino acid sequence of SEQ ID NO: 132 encoded by the DNA sequence of SEQ ID NO: 150; mAb DM4 has a heavy chain with the amino acid sequence of SEQ ID NO: 134 encoded by the DNA sequence of SEQ ID NO: 147, and a light chain with the amino acid sequence of SEQ ID NO: 135 encoded by the DNA sequence of SEQ ID NO: 148.

An antibody of the invention can be prepared by recombinant expression of immunoglobulin light and heavy chain genes in a host cell. Mammalian host cells are preferred, e.g., CHO cells, NSO cells, SP2/0 cells and COS cells. CHOK1SV cells, which utilize the glutamine synthetase (GS) gene expression system, are particularly preferred (See, de la Cruz Edmonds. et al, *Mol Biotechnol.* 2006; 34(2):179-90 and US 20070105771). Antibodies can be recovered from the host cell and/or the culture medium using standard purification methods.

Pharmaceutical Compositions

An antibody of the invention is preferably incorporated into a pharmaceutical composition suitable for administration to a subject. Such compositions comprise a therapeutically effective amount of an antibody of the invention in a pharmaceutically acceptable carrier, diluent, or excipient. Such pharmaceutical compositions are designed to be appropriate for the selected mode or route of administration, and pharmaceutically acceptable diluents, carriers, and/or excipients such as dispersing agents, buffers, surfactants, preservatives, solubilizing agents, isotonicity agents, stabilizing agents, and the like are used as appropriate. Such compositions can be designed in accordance with conventional techniques as disclosed, for example, in Remington, *The Science and Practice of Pharmacy*, 19$^{th}$ Edition, Gennaro, Ed., Mack Publishing Co., Easton, Pa. 1995. Suitable carriers for pharmaceutical compositions include any material which, when combined with an antibody of the present invention, retains the molecule's activity and is non-reactive with the subject's immune system.

Preferably, an antibody of the present invention is in an aqueous formulation for subcutaneous, intravenous, intraperitoneal, or intramuscular administration. The therapeutically effective amount of antibody present in the formulation is determined by taking into account the desired dose volumes and mode(s) of administration. From about 1 mg/ml to about 250 mg/ml, preferably from about 20 mg/ml to about 100 mg/ml, is an exemplary antibody concentration in the formulation.

An aqueous formulation is prepared comprising an antibody of the invention in a pH-buffered solution. The buffer of the formulation has a pH in the range of from about 5.5 to about 7.0, preferably a pH of about 6.0 to about 6.5. Examples of buffers that will control the pH within this range include acetate (e.g. sodium acetate), citrate (e.g., sodium citrate), and other organic acid buffers. The buffer concentration can be from about 10 mM to about 30 mM, preferably about 10 mM, depending, for example, on the buffer and the desired isotonicity of the formulation. The preferred buffer is sodium citrate (about 10 mM), pH of about 6.0 to about 6.5.

A surfactant can also be added to the antibody formulation. The amount of surfactant added is such that it reduces aggregation of the formulated antibody and/or minimizes the formation of particulates in the formation and/or reduces adsorption. Preferably, Polyoxyethylene-sorbitan-20-monooleate (also known as polysorbate 80 and Tween 80), can be present in the formulation in an amount from about 0.005% to about 0.05%, more preferably about 0.01% to about 0.03%, by weight of the total compositon.

In preferred embodiments, the formulation contains a tonicifying amount of a salt such as sodium chloride. From about 50 to about 150 mM is an exemplary concentration of sodium chloride in the formulation.

Therapeutic Uses

The term "renal renin-angiotensin system (RAS) inhibitor" refers to a compound or a composition having the ability to reduce the amount or the biological activities of angiotensin (Ang) II. The term is inclusive of angiotensin converting enzyme (ACE) inhibitors, Ang II receptor antagonists (also known as "Ang II receptor blockers"), and a combination thereof.

The term "angiotensin-converting enzyme (ACE) inhibitor" refers to a compound or a composition having the ability to inhibit the cleavage of the N-terminal decapeptide Ang I to the vasoactive octapeptide Ang II, e.g., lisinopril and captopril.

The terms "angiotensin (Ang) II receptor antagonist" and "Ang II receptor blocker" refer to a compound or a composition having the ability to inhibit the vasoconstuction and profibrotic effects of endogenous Ang II via blocking the binding of angiotensin II to the AT1 receptor, e.g., losartan and irbesartan.

Accumulation of components of the extracellular matrix (ECM) or the replacement of normal cellular material with ECM components in a wide variety of cells, tissues, and organs can result in disease-producing fibrosis. Progressive fibrosis can be fatal, leading to end-organ failure in multiple organs, such as, the kidney. Preclinical and clinical data indicate that TGF-Beta 1 is a major contributor to ECM deposition in interstitial fibrosis, and is involved in the initiation and progression of a number of fibrotic diseases or disorders, for example, renal fibrosis, hepatic fibrosis, and pulmonary fibrosis.

Both TGFβ and Ang II have been implicated in fibrotic diseases, particularly fibrotic renal diseases, and Ang II may mediate its effects through TGFβ. Thus, antibodies of this invention may be combined with or used in association with other therapeutic agents such as, e.g., ACE inhibitors, and/or Ang II receptor blockers. Preferably, antibodies of the invention are administered in combination with ACE inhibitors, e.g., lisinopril and captopril, and/or Ang II receptor blockers, e.g., losartan and irbesartan, for treating chronic kidney disease in a patient.

In another embodiment, an antibody or an antigen-binding fragment thereof of the invention can be also used for treating cellular proliferative diseases because TGF-β1 not only has transforming potential, but can also drive malignant progression, invasion, and metastasis both in vitro and in vivo. Examples of hyperproliferative diseases or disorders, include, e.g., without limitation, a neoplasm of the colon, bone, breast, liver, pancreas, the lymphatic system, skin, spleen, thorax, and urogenital system.

As is well known in the medical arts, dosages for any one subject depend on many factors, including the patient's size, body surface area, age, the particular compound to be administered, sex, time and route of administration, general health, and other drugs being administered concurrently. A typical daily dose, i.e., an effective amount, for an antibody or antigen-binding fragment thereof of the present invention can be, for example, in the range of from about 0.1 to about 1000 mg; however, doses below or above this exemplary range are envisioned, especially considering the aforementioned factors. Preferably, 1 to 250 mg of antibodies of the present invention, more preferably, 5, 10, 15, 20, 25, 30, 35, 40, 45, 50, 55, 60, 80, 100, 120, or 240 mg of antibodies of the present invention, can be subcutaneously administered to a patient with a single-dose injection, followed by a monthly injection with the same or lower amount.

EXAMPLES

Example 1

Construction and Screening of Fab Fragments Using CDRs and Human Frameworks

Standard approaches to characterizing and synthesizing antibody variable region CDR libraries of single mutations are used (see, e.g., Wu et al, 1998 PNAS 95:6037-42). Libraries are constructed in bacteriophage M13 expression vectors containing antibody light chain and heavy chain genes composed of human constant region and variable region framework sequences described herein together with CDR sequences of the invention. In some cases, the target CDR is first deleted prior to annealing the nucleotides. Codon based mutagenesis for oligonucleotide synthesis to yield CDR sequences of the invention is employed.

Libraries are initially screened by capture lift to identify the highest affinity variants. The capture lift procedure (Watkins, 2002 Methods Mol. Biol. 178:187-93) is art known and described in WO/0164751 and US2002/0098189. Subsequently, desired clones are further characterized by titration on immobilized antigen in an ELISA and a cell proliferation potency assay as described herein. Following such screening, dissociation constants ($K_d$), association rates ($K_{on}$) and dissociation rates ($K_{off}$), are determined for a clone of interest.

To identify potential antibody binding compositions comprising embedding donor CDRs of the invention, libraries of synthetic CDRs are inserted into a deletion template as described herein or art known. Standard mutagenesis techniques (Kunkel, 1985 PNAS 82:488-92) are employed to replace a particular CDR using a pool of mutagenic oligonucleotides. Typically, CDR positioning within a framework is accomplished using the system as defined by Kabat with the exception of CDRH 1, which is the sum of Kabat and Chothia definitions. Mutagenic oligonucleotides are annealed to an uridinylated phage template in which the corresponding CDR is deleted.

Annealing is accomplished by incubating a reaction at 85° C. for 5 minutes followed by slow cooling to 20° C. over the course of 45 minutes. Annealed samples are placed on ice, T4 DNA polymerase and T4 DNA ligase are added to generate double stranded DNA, and the reaction is incubated for 5 minutes at 4° C. followed by 90 minutes at 37° C. The reaction is phenol extracted, ethanol precipitated and the resulting DNA electroporated into DH10B cells. XLOLR cells are added to the reaction to allow phage amplification before the libraries are plated. Phage stocks are prepared by the addition of 8 ml of growth medium to the plates followed by incubation at 4° C. for a minimum of 4 hours. The phage-containing medium is harvested and clarified by centrifugation and sodium azide (0.02%) is added as a preservative.

Initial screening of the libraries is done by plaque lifts as described in Watkins, et al 1998 Anal Biochem 256: 169-77; and Watkins, 2002 Methods Mol. Biol., 178:187-93. Filters containing expressed Fabs from individual plaques bound to immobilized anti-human kappa antibody are sequentially incubated with biotinylated TGF-beta-1 (bio-TGF-beta-1), Neutravidin-alkaline phosphatase (NA-AP), with brief washes in between. Clones of interest are sequenced and further characterized by ELISA. The ELISA generally used Costar 3366 microtiter plates coated overnight at 4° C. with 0.4 ug/ml TGF-beta-1, TGF-beta-2 or TGF-beta 3. Plates are subsequently washed 2× times prior to the addition of 100 uL of blocking solution (10 mg/ml BSA in wash buffer) into each well. Dilutions of Fabs are incubated in the coated wells for 1.5 h at 22° C. After washing, an anti-human kappa-alkaline phosphatase conjugate is added and incubated for 1 hour at 22° C. A colometric substrate is added after extensive washing and absorbance is at A560 is measured to identify positive clones.

Assaying Fabs by ELISA

In one non-limiting example, an ELISA is employed that uses Costar 3366 microtiter plates coated overnight at 4° C. with 0.4 ug/ml TGF-beta 1, TGF-beta 2, or TGF-beta 3 (TGF-beta 1 (R&D Systems, Cat # 240-B/CF, 239 ug/ml), TGF-beta 2 (RDI, Cat # RDI-1035, 50 ug/ml) and TGF-beta 3 (RDI, Cat # RDI-1036/CF, 50 ug/ml) diluted to 0.4 ug/mL in coating buffer). The plate is subsequently washed (2×) prior to the addition of 100 uL of Blocking solution (10 mg/ml BSA in wash buffer) into each well. Dilutions of Fabs of the invention are incubated in the coated wells (1.5hr at 22° C.). After washing, an anti-human kappa-alkaline phosphatase conjugate is added and incubated (1 hour at 22° C.). A colometric substrate is added after extensive washing and absorbance is measured at A560.

In another example, binding compositions of the invention are tested in a competitive ELISA assay. Typically, a solution phase assay is performed in which a compound that might compete with an antigen for binding to a binding composition, such as an antibody, is combined first with the antibody in solution phase, then the degree of binding of the antibody with the antigen is subsequently measured.

Materials:

Carbonate coating buffer consists of 50 mM sodium carbonate pH 9.6. Antigens are TGF-beta 1 (R&D Systems, Cat #240-B/CF, 239 ug/ml), TGF-beta 2 (RDI, Cat # RDI-1035, 50 ug/ml) and TGF-beta 3 (RDI, Cat # RDI-103 6/CF, 50 ug/ml) diluted to 0.4 ug/mL in coating buffer. Wash buffer consists of 0.02 M Tris pH 7.4, 0.15 M NaCl, 0. 1% Tween 20 and blocking solution of 10 mg/ml BSA (Sigma A-4503) dissolved in wash buffer. Proteins used as positive controls are mouse-anti-human TGF-beta 1, 2, or 3 (R&D Systems, cat#1D11), mouse-anti-human TGF-beta 2 (R&D Systems, cat# BAF302) and mouse-anti-human TGF-beta 3 (R&D Systems, cat# BAF243), which are diluted to 1ug/ml in block buffer. The detection antibody conjugate used is anti-mouse kappa-peroxidase conjugate (Southern Biotech, cat# 1050-05), at a working concentration of 1:2000 in blocking solution. The substrate used for the color reaction is 0-phenylenediamine (OPD) tablets (Sigma cat# P-6912), which is dissolved in substrate buffer: 0.1 M $Na_2HPO_4$, pH to 5.0 with 0.05 M citric Acid. The OPD substrate working solution (i.e., the volume for one 196-well-plate) is freshly made prior to each plate development by dissolving 1×5 mg OPD tablet in 12.5 mL of substrate buffer followed by the addition of 5 ul of 30% $H_2O_2$.

Protocol:

A single 96 well plate is coated with antigen (TGF-beta 1, 2, or 3 at 0.4 ug/ml and dispense 50 uL per well) and then sealed with adhesive tape before storage (16-20 hours at 4° C.). The plate is subsequently washed (2×) in wash buffer (described above) before adding 100 uL of blocking solution (10 mg/ml BSA in wash buffer) into each well. After incubation (approximately 1 hour at 22° C.), the plate is washed (2×) with wash buffer. Then, 100 uL of either sample (diluted in buffer) or control (diluted in PBS) is added to each well and incubated (1.5 hours at 22° C.). After incubation, the plate is washed (6×) with wash buffer before adding 100 uL per well of either anti-mouse kappa-peroxidase conjugate (diluted to 1:2000 in Blocking solution) or SA-HRP (diluted 1:10,000 in blocking solution). The test samples are left to incubate (1 hour at 22° C.) before adding 100 uL of OPD substrate to each well. After color development (approximately 10 minutes), the 96-well plate is measured at an absorbance of 490 nm.

Successful results under such conditions are Fab embodiments that produce an absorbance greater than 1.6 units at 490 nm with TGF-beta 1 but show significantly lower values with TGF-beta 2 and TGF-beta 3 thus demonstrating specific and/or selective binding for TGF-beta 1.

Assaying MAbs in a Cell-Based Assay

To test the ability of a binding composition of the invention to neutralize TGF-beta bioactivity and to neutralize a particular TGF-beta isoform, one can adapt the HT-2 cell proliferation assay of Tsang, et al., (1995 Cytokine 7:389-97). The HT-2 cell proliferation assay is utilized to determine the in vitro potency of Fab and mAb compositions. Briefly, HT-2 cells proliferate in the presence of IL-4 but undergo apoptosis in the presence of TGF-beta. The TGF-beta induced cell death is prevented by the addition of a TGF-beta 1 neutralizing Fab or mAb.

The human cell line HT-2 proliferates in response to IL-4 but the IL-4-induced-proliferation is inhibited by TGF-beta 1, TGF-beta 2, or TGF-beta 3. Consequently, a binding composition that is specific and/or selective for TGF-beta 1 is neutralizing if it prevents the normal inhibitory effect that TGF-beta 1 has on IL-4-induced HT-2 cells. Accordingly, IL-4-induced cell proliferation should proceed unconstrained if sufficient TGF-beta 1-specific binding composition is added to a mixture of HT-2 cells containing TGF-beta 1. Consequently, the dose response neutralizing capability of binding compositions of the invention is assessed using the HT-2 assay in the presence of particular TGF isoforms and the IL-4 proliferation signal. The degree of cell proliferation is assessed using a commercial colorimetric cell proliferation measure (e.g., CellTiter 96® AQueous One Solution Cell Proliferation Assay from Promega).

HT-2 cells are maintained in RPMI 1640 supplemented with 10% FBS, penicillin/streptomycin at 100 U/ml and 100 ug/ml respectively, 50 uM beta-mercaptoethanol and 10 ng/ml human IL-2 (R&D Systems). Cells are centrifuged at 1000 RPM in a Jouan CR422 centrifuge and re-suspended in PBS. After two washes with PBS, cells are finally re-suspended at $0.15 \times 10^6$ cells/ml in Assay Media which consists of phenol red-free RPMI 1640 supplemented with 2% FBS, penicillin/streptomycin at 100 U/ml and 100 ug/ml respectively and 50 uM beta-mercaptoethanol. To each well of a 96 well plate is added 50 ul of cells in Assay Media. Before adding test mAbs to cell bioassay, varying concentrations of mAb are pre-incubated with 300 pg/ml TGF-beta 1, TGF-beta 2, or TGF-beta 3 (in Assay Media). Following a 30 min incubation, 50 ul of the TGF-beta/Fab mixture is added to the cells, followed immediately thereafter by 50 ul of Assay media containing 45 ng/ml murine IL-4 (15 ng/ml final). After an incubation of 20-48 hr, 35 ul of CellTiter 96 Aqueous solution (Promega Corp) is added. After a further 2 to 3 hr incubation (37° C. in a humidified, 5% CO2 atmosphere), the assay is quantitated by analysis on an ELISA plate reader at 490 nM using the CellTiter 96® colorimetric assay (the quantity of formazan product generated and as measured by the amount of 490nm absorbance is directly proportional to the number of living cells in culture). Model data of neutralizing TGF-β1 induced cell death are shown below in Table 2.

TABLE 2

HT-2 In Vitro Cell Bioassay: An HT-2 cell proliferation assay is utilized to determine in vitro potency of Fab and mAb binding compositions of the invention. HT-2 cells proliferate in the presence of IL-4 but undergo apoptosis in the presence of TGF-beta1. A TGF-beta1 induced cell death is prevented by the addition of a TGF-beta neutralizing compositon (such as, e.g., a Fab or mAb of the invention). In comparison to the murine IgG1 FAb #2471, binding compositions of the invention show at least a greater than 100-fold or more improvement in neutralization potency in preventing TGF-beta1 induced cell death. The IC50's for mAb compositions range from approximately 0.1-1.0 ng/ml (the IC50 of mAb 2471 is approximately 0.1 µg/ml).

| Anti-TGF - β1 mAb Binding Compositions | Fold Improvement in IC50 relative to mAb2471 |
|---|---|
| 21D1 | 106.8 + 16.1 |
| DM4 | 391.0 + 5.2 |
| DM7 | 140.0 + 29.2 |
| C27 | 401.0 + 132.3 |
| 23A3 | 234.2 + 37.9 |

Measuring Kinetic Constants for Fabs

A KinExA 3000 instrument (Sapidyne Inst. Inc.) is used to measure binding kinetics. Briefly, an antigen is covalently coupled to alzactone beads and the binding of a free Fab binding composition of the invention to the beads is detected on the instrument. To measure Kd, individual tubes containing 20 pM of Fab (200 pM for the mAb) with decreasing serially diluted antigen (0-250nM), is incubated for 1-6 days at 25° C. in PBS containing 1% BSA, 0.02% azide and 0.01% Tween20. After the incubation, free Fab in each equilibrated sample is determined on the KinExA 3000 according to the manufacturer's instructions. $K_d$ values are determined using KinExA 3000 software.

To measure $k_{on}$, individual Fabs at 2 nM are mixed with 0-240 nM of antigen using the injection method according to the manufacturer's instructions, and the unbound Fab is detected. The resulting data is used to calculate the $k_{on}$ with KinExA 3000 software. The $k_{off}$ is calculated by using the formula $K_d = k_{off}/k_{on}$.

Measuring Kinetic Constants for Mabs

Alternate methods of measuring kinetic constants are known, for example: affinity of a binding composition for human TGF-beta 1 (R&D Systems, Cat #240-B/CF), TGF-beta 2 (RDI, Cat # RDI-1035) and TGF-beta 3 (RDI, Cat # RDI-1036/CF) is measured using a BIAcore® 2000 instrument. The BIAcore® utilizes the optical properties of surface plasmon resonance to detect alteration in protein concentration of interacting molecules within a dextran biosensor matrix. Except as noted, all reagents and materials are purchased from BIAcore® AB (Upsala, Sweden). All measurements are performed at room temperature. Samples are dissolved in HBS-EP buffer (150 mM sodium chloride, 3 mM EDTA, 0.01% (w/v) surfactant P-20, and 10 mM HEPES, pH7.4). Recombinant Protein A is immobilized on all four flow cells of a CM4 sensor chip at a level of 400-450 response units (RUs) using an amine coupling kit.

Binding is evaluated using multiple analytical cycles. Each cycle is performed at a flow rate of 50 µL/minute and consists of the following steps: injection of 12 µL of an antibody binding composition at 0.5 µg/mL, injection of 250 µL of TGF-beta 1 (starting at 5 nM and using two-fold serial dilutions to 0.13 nM for each cycle, with two injections for each concentration) followed by either a short (5 minutes) or long (120 minutes) delay for dissociation, and regeneration using two injections of 50VL of 10 mM glycine hydrochloride, pH1.5. Association and dissociation rates for each cycle are determined by fitting of the biosensor data using to a simple association model using ClampXP (Center for Biomolecular Interaction Analysis, Univ. of Utah) to extract the $k_{on}$ and $k_{off}$ rate constants; the equilibrium binding constant Kd is calculated using the relationship $K_d = k_{off}/k_{on}$. Model data for invention compositions are in Table 3 shown below.

TABLE 3

Binding affinity and kinetic measurements for Fabs and mAbs of the invention. Equilibrium ($K_d$) and kinetic ($k_{on}$) binding parameters are determined using Kinexa ($k_{off}$ is calculated from $K_d$ and $k_{on}$). Equilibrium and kinetic binding properties of mAbs are determined using Biacore. The equilibrium binding constant $K_d$ is calculated from the determined $k_{on}$ and $k_{off}$. Comparison is to murine IgG1 Fab #2471. Due to the very slow dissociation, the $k_{off}$ for 21D1 and DM7 is the upper limit detectable, and are likely much slower, and therefore, the $K_d$ values calculated are also upper limits. Values are the average of repeat measurements (n = 3-4).

| | Fab Binding Data (Kinexa) | | | Mab Binding data (Biacore) | | |
|---|---|---|---|---|---|---|
| | $k_{on}$ $(M^{-1}$ $s^{-1})$ $(\times 10^{-6})$ | $k_{off}$ $(sec^{-1})$, calc, $(\times 10^6)$ | $K_d$ (pM) | $k_{on}$ $(M^{-1}$ $s^{-1})$ $(\times 10^{-7})$ | $k_{off}$ $(sec^{-1})$, $(\times 10^5)$ | $K_d$ (pM) (calc) |
| 2471 | 1.7 | 664 | 406 | nd | nd | nd |
| 21D1 | 4.0 | 3.4 | 0.9 | 1.3 ± 0.1 | <0.6 ± 0.6 | <0.5 ± 0.5 |
| DM4 | 4.2 | 5.1 | 1.2 | 1.6 ± 0.3 | 1.4 ± 0.9 | 0.9 ± 0.4 |

TABLE 3-continued

Binding affinity and kinetic measurements for Fabs and mAbs of the invention. Equilibrium ($K_d$) and kinetic ($k_{on}$) binding parameters are determined using Kinexa ($k_{off}$ is calculated from $K_d$ and $k_{on}$). Equilibrium and kinetic binding properties of mAbs are determined using Biacore. The equilibrium binding constant $K_d$ is calculated from the determined $k_{on}$ and $k_{off}$. Comparison is to murine IgG1 Fab #2471. Due to the very slow dissociation, the $k_{off}$ for 21D1 and DM7 is the upper limit detectable, and are likely much slower, and therefore, the $K_d$ values calculated are also upper limits. Values are the average of repeat measurements (n = 3-4).

| | Fab Binding Data (Kinexa) | | | Mab Binding data (Biacore) | | |
|---|---|---|---|---|---|---|
| | $k_{on}$ ($M^{-1}$ $s^{-1}$) ($\times 10^{-6}$) | $k_{off}$ ($sec^{-1}$), calc, ($\times 10^6$) | $K_d$ (pM) | $k_{on}$ ($M^{-1}$ $s^{-1}$) ($\times 10^{-7}$) | $k_{off}$ ($sec^{-1}$), ($\times 10^5$) | $K_d$ (pM) (calc) |
| DM7 | 4.5 | 2.3 | 0.5 | 1.3 ± 0.3 | <0.7 ± 0.4 | <0.5 ± 0.4 |
| C27 | 4.1 | 17 | 4.2 | 1.3 ± 0.1 | 0.8 ± 0.5 | 0.6 ± 0.4 |
| 23A3 | 4.8 | 19 | 4.0 | 1.9 ± 0.4 | 1.0 ± 0.8 | 0.8 ± 0.6 |

Determination of Mab Specificity

BIAcore methods are used to determine the ability of invention mAb compositions to bind other entities, specifically the latent form of TGF-beta 1 or TGF-beta 3. All measurements are performed at room temperature. Samples are dissolved in HBS-EP buffer (150 mM sodium chloride, 3 mM EDTA, 0.01% (w/v) surfactant P-20, and 10 mM HEPES, pH7.4). Recombinant Protein A is immobilized on all four flow cells of a CM4 sensor chip at a level of 400-450 response units (RUs) using an amine coupling kit.

Binding is evaluated using multiple analytical cycles. Each cycle is performed at a flow rate of 100 μL/minute consisting of the following steps: injection of 15 μL of an antibody binding composition at 1 μg/mL, injection of 250 μL of either 5 nM TGF-beta 1, 5 nM latent TGF-beta 1, or 5 nM TGF-beta 3 followed by a short delay (5 min) for dissociation, and regeneration using two injections of 50 μL of 10 mM glycine hydrochloride, pH1.5. The amount of signal after capturing first the Mab, and then the ligand, are determined using the instrument control software. Since the signal is proportional to the mass of protein captured, the stoichiometry of the captured ligand is readily calculable (Table 4).

TABLE 4

Binding of TGF-beta 1, latent-TGF-beta 1 and TGF-beta 3 to Mabs (tested at 5 nM ligand).

| | Stoichiometry of ligand binding | | |
|---|---|---|---|
| Mab | TGF-β1 | Latent TGF-β1 | TGF-β3 |
| 21D1 | 1.29 | 0.05 | 0.16 |
| DM4 | 1.55 | 0.03 | ND |
| DM7 | 1.23 | 0.04 | 0.54 |
| C27 | 1.74 | 0.08 | ND |
| 23A3 | 1.63 | 0.07 | 1.26 |

Specificity for TGF-beta 1

Affinities of binding composition mAbs for TGF-β3 are determined using BIAcore methods. All measurements are performed at room temperature. Samples are dissolved in HBS-EP buffer (150 mM sodium chloride, 3 mM EDTA, 0.01% (w/v) surfactant P-20, and 10 mM HEPES, pH7.4). Recombinant Protein A is immobilized on four flow cells of a CM4 sensor chip at a level of 400-450 response units (RUs) using an amine coupling kit. Binding is evaluated over multiple analytical cycles. Each cycle is performed at a flow rate of 100 μL/minute consisting of the following steps: injection of 15 μL of an antibody binding composition at 0.5 μg/mL, injection of 250 μL of TGF-β3 (starting at 5 nM and using two-fold serial dilutions to 0.13 nM for each cycle, with two injections for each concentration) followed by a short (5 minutes) delay for dissociation, and regeneration using two injections of 50VL of 10 mM glycine hydrochloride, pH1.5.

Affinities are determined based upon the equilibrium signal as reached at varying TGF-β3 concentrations by measuring the average signal during the last 10 seconds of the TGF-β3 injections, and then fitting the resulting signals at all of the TGF-β3 concentrations to a simple binding equilibrium model in SCRUBBER (Center for Biomolecular Interaction Analysis, Univ. of Utah). Model data determined for tested human mab composition of the invention of $K_d$ and specificity calculated by dividing the $K_d$ for TGF-β3 binding by the $K_d$ for TGF-β1 binding (herein) is shown below in Table 5.

TABLE 5

Affinity and relative specificity of binding composition tested mAbs for TGF-beta 3 binding. Errors, where shown, represent the standard deviation from multiple repeat measurements (n = 3).

| Mab | $K_d$ (TGF-β3), nM | Specificity ($K_{d,β3}/K_{d,β1}$) |
|---|---|---|
| 21D1 | 4.90 | 9800 |
| DM4 | 0.53 ± 0.01 | 621 |
| DM7 | 1.16 ± 0.18 | 2320 |
| C27 | 2.20 | 3670 |
| 23A3 | 0.66 ± 0.04 | 1050 |

Example 2

Hepatic Fibrosis Bile Duct Ligation In Vivo Model

A bile duct ligation model is utilized in a manner similar to that reported by Arias et al (BMC Gastroenterology 3(29), 2003) to evaluate in vivo efficacy of anti-TGF-β1 therapy. Briefly, male Sprague Dawley rats (250-300 g) are anesthetized with isoflurane (2-3%) inhalation for effect. The abdomen is shaved and scrubbed with betadine and 70% ethyl alcohol. Under sterile conditions, a midline incision (~4 cm) is made and the common bile duct is isolated and ligated with 6-0 surgical silk in two positions, approximately 1 cm apart and then transected between ligatures. The abdominal wall is closed with 4-0 silk suture and the skin stapled together. Administration of an anti-TGF-β1 composition and isotype mouse control mAb (IgG) are commenced on the day of surgery and every 7 days thereafter. At 4 and 12 days post-surgery, rats are euthanized and serum liver enzymes, complete blood count, and liver histology (trichrome and H&E stains) are processed to determine effect of treatment.

Example 3

Lung Fibrosis In Vivo Model

A number of models are available in evaluating the in vivo efficacy of anti-TGF-beta compositions on lung fibrosis. For example, a bleomycin model applied in the manner reported by Pittet, et al (JCI 107, 1537-1544, (2001) is used to assess amelioration in an anti-TGF-beta approach. Another model is the respiratory reovirus 1/L model (see, e.g., Bellum et al., Am. J. Pathol, 150, 2243; or London et al, Clin. Immunol.

103, 284; and London et al, Exp. Mol. Pathol, 72, 24-36). Briefly, using mice, on day 1, Reovirus 1/L, i.n. $1\times10^7$ pfu (30 ul total) is applied via the nostril followed on days 3, 7, 12 with varying concentrations of anti-TGF-beta binding composition of the invention or an isotype control mAb as described herein or art known. Animals are monitored during the course of treatment for signs of respiratory distress, weight loss, and mortality. On day 14 after initiation of treatment, animals are euthanased and lung samples prepared for histopathological examination (H/E) to assess the development and/or progression of lung disease (with hydroxyproline content analyzed for measurement of fibrosis).

Example 4

Anti-Thy.11 Glomerulonephritis In Vivo Model

The rat anti-Thy1.1 model is a well-established model of mesangioproliferative glomerulonephritis (see, e.g., Morita, et al., 1998 Am J Kidney Dis 31:559-73; Bagchus, et al., 1986 Lab. Invest. 55:680-7 and Yamamoto & Wilson 1987 Kidney Int. 32:514-25) in which injection of an antibody directed against the Thy antigen located on the surface of mesangial cells induces mesangiolysis followed by a phase of over compensatory proliferation of mesangial cells resulting in elevated levels of urinary protein (proteinuria). The anti-Thy1.1 nephritis model resembles human IgA nephritis or Henoch-Schonlein purpura in many aspects (O'Donoghue, et al., 1991 J Clin Invest 88:1522-30) and it has been used to test potentially therapeutic approaches to kidney disease by determining the ability of test compositions to effect dose-related decreases in proteinuria (see, e.g., Burg, et al., 1997 Lab Invest 76:505-16; Johnson, et al., 1995 Kidney Int 47:62-9).

To test binding compositions of the invention in such a model, individually marked, male Sprague Dawley rats (200-260 grams; approximately 9 weeks of age) are acclimated for five days pre-treatment with free access to food and water on a standard diet. A pre-urinary protein determination is made at pre-treatment day-5. Rats are given an individual identification by marking on the tail with a colored marker as well as ear tagged prior to being bled by retro-orbital, and randomized into 5 groups based on body weight at day 1.

The study is performed blinded to the treatment groups and unblinded at the end of the study. Groups recieve either 1.25 mg of anti-Thy1.1 mAb or PBS as a control injection via the penile vein on day 0. Binding compositions are prepared and purified under standard conditions or as described herein. The control mouse IgG1 mAb (11513) is protein A purified material resuspended in PBS pH7.2 and is purchased from Harlan Bioproducts for Science, Indianapolis, Ind. 46229-0176.

Mouse anti-Thy 1.1 is produced in 2×10 L cultures of mouse hybridoma. Conditioned media is combined, concentrated to 18× and subsequently purified. Approximately, 764 mLs of the concentrated harvest supernatant is mixed with 1.5M Glycine/3.0M NaCl pH 8.9 and applied to a virgin, 137 ml Protein A Sepharose column that is pre-equilibrated in 1.5M Glycine/3.0M NaCl pH 8.9. The Protein A column is then ished with 1.5M Glycine/3.0M NaCl pH 8.9. The column is eluted with 100 mM Citric Acid pH 3.0. Selected fractions of eluate that correspond to IgG are pooled, adjusted to pH 7.4 with 1M NaOH, and applied to a 318 ml Pharmacia Superdex 200 column equilibrated in PBS, pH 7.4sodium chloride. The peak corresponding in size to IgG is pooled, aliquoted and stored at –20° C.

One hour after anti-Thy1.1 mAb administration, animals are dosed subcutaneously with isotype or anti-TGF-beta 1 antibody compositions of the invention. Antibodies are again dosed on day 7, animals are tested in the following four treatment groups:

1) Shams; PBS injection
2) Anti-thy1.1 with Isotype control antibody at ~12.5 mg/kg or 2.5 mg/dose
3) Anti-thy1.1 with DM4 antibody at 5 mg/kg, or 1 mg/dose
4) Anti-thy1.1 with DM7 antibody at ~12.5 mg/kg, or 2.5 mg/dose
5) Anti-thy1.1 with C27 antibody at ~12.5 mg/kg, or 2.5 mg/dose Rats are placed into metabolic cages for a 24 hr time period on days—5 and 13. On day 14, rats are sacrificed by $CO_2$ and bled via cardiac puncture to obtain blood for analysis. The left kidney is fixed with 4% Paraformaldehyde in PBS and stored in 70% ethanol for later histological analysis. If any rat becomes moribund, it is sacrificed ($CO_2$) and processed for urinary protein and blood urea nitrogen concentrations. Urinary protein and blood urea nitrogen (BUN) concentrations are analyzed on a HITACHI 911 automatic analyzer with controls from Biorad according to the manufacturers instructions.

Model data in Table 6 below show the binding compositions of the invention have a significant ability to attenuate renal damage in vivo and to reduce the elevated protoneuria associated with anti-Thy1.1 mAb induced renal damage.

TABLE 6

| Thy1.1 Ab | Ab group | Study No. | Dose (mg) | Day 14 Urine Protein (mg/24 hrs) | | % of Control IgG | |
|---|---|---|---|---|---|---|---|
| | | | | AVG. | SE | AVG. | SE |
| 2.5 mg/kg i.v. | 21-D1 | HS4606 | Sham | 7.0 | 3.0 | | |
| | | | 0 | 73.4 | 9.5 | 100.0 | 14.3 |
| | | | 0.1 | 65.7 | 7.3 | 88.5 | 11.1 |
| | | | 0.5 | 35.2 | 6.2 | 42.5 | 9.3 |
| | | | 1 | 29.1 | 3.8 | 33.3 | 5.8 |
| 2.5 mg/kg i.v. | DM4 | HS4607 | Sham | 9.9 | 2.3 | | |
| | | | 0 | 67.2 | 6.5 | 100.0 | 11.3 |
| | | | 0.1 | 54.7 | 6.2 | 78.1 | 10.8 |
| | | | 0.5 | 49.7 | 6.2 | 69.4 | 10.7 |
| | | | 1.0 | 28.9 | 4.7 | 33.2 | 8.2 |

Example 5

Epitope Mapping of TGF-β1 Binding Compositions

A combination of H/Dex and chemical labeling are used to map epitopes of TGF-β1 binding compositions of the invention such as, for example, antibodies. As both H/D exchange and chemical modification depend on solvent accessibility to amino acid residues, changes in solvent accessibility after formation of a binding composition:TGF-beta 1 complex can be used to identify residues involved in antibody binding. Subsequent to H/D exchange or chemical modification, proteolytic digestion into peptide cleavage fragments of the formerly bound antigen permits molecular weight comparisons between fragments (using LC/MS) to determine which amino acid residues are blocked from H/D exchange or chemical modification after binding complex formation.

Protein Surface Chemical Labeling 15 µg aliquots of 1 mg/mL TGF-β1 in 4 mM HCl solution are transferred into plastic vials, to which 180 µg of either a control or a TGF-β1 antibody composition of the invention is added (TGF-β1/antibody=½ in molar ratio). Phosphate buffered saline (PBS) is added into each vial to a final volume of 150 µL and the solutions are allowed to incubate (to permit formation of a binding complex) at ambient temperature for at least 10 min before protein surface labeling. For chemical labeling, 7.5 µL of a 5 mg/mL acetic acid hydroxylsuccinimide ester (AHSE) solution is added in each complex vial and the mixtures are then incubated at ambient temperature (AHSE/antibody=200/1 in molar ratio). At varying times (e.g., 10, 20, and 60 min), 50 µL of the mixture solution is quenched by mixing with 50 IL of 1 mg/mL K in 0.1 M tris buffer, pH 8.0. The solution is directly analyzed by LC/MS (as described herein). The remaining solution of each sample is treated with 3-5 µL of 50 mg/mL DTT solution at 37° C. (10-15 min) to reduce the disulfide bonds of mature TGF-β1.

The reduced protein solution is subsequently treated with 3 µL of 0.1 mg/mL chymotrypsin solution at 37° C. for 2-3 hours, and then treated with 1 µL of 0.25 mg/mL Glu-C solution at 37° C. for another 2-3 hours. This reaction is quenched by adding 0.5 µL of glacial acetic acid, and then analyzed by LC/MS, using a Waters 2795 HPLC and Micromass LTC Premier Mass spectrometer. The HPLC used a Zorbax, SB C18, 2.1×50 mm, at ambient temperature, and proteins and peptides are eluted with an acetonitrile gradient in 0.15% formic acid; a 14 minute run time is used for the intact protein, and a 75 minute run time is used for proteolytic digests.

For lysine (K) residues on the TGF-β1 surface or either within or structurally near the epitope, acetylation of the K amino group is blocked (either partially or completely) after a test composition binds TGF-β1. Comparing the extent of acetylation between a peptide from a complexed (TGF-P1+ antibody that binds TGF-β1) or uncomplexed (TGF-β1+ control antibody that does not bind TGF-β1) sample allows one to identify amino acid residues blocked from acetylation by the formation of the binding complex. One model of acetylation data obtained under such an LC/MS analysis is shown below in Table 7.

Given such model data, differences between the TGF-β1: antibody complexes and controls are discernable for several TGF-β1 peptide fragments, especially as shown for short periods of acetylation (e.g., 10 min). Fragments encompassing residues 31-39, 33-43, 53-62, and 91-112 demonstrate such discernable differences. Both fragments 31-39 and 33-43 comprise the K37 residue. Fragment 22-32, which comprises K26 & K31, shows no significant difference over controls, thus the acetylation differences of fragment 31-39 are attributable to blocking K37 from acetylation after formation of the antigen: antibody complex.

Fragments 53-62 and 91-112 exhibit persistent differences over the tested range and for each antibody tested. Fragment 53-62, shows decreased differences in the upper range of acetylation (60 min), however, under lower AHSE/antibody ratio conditions, such differences remain unchanged throughout the range. Not being bound by theory, one interpretation of such data is that K60 is not directly involved in antigen: antibody binding but that its proximity to the binding complex is sufficiently close to block accessibility of AHSE to the K60 residue, thus blocking acetylation. Alternatively, however, K60 can comprise the epitope defined by the tested antibody.

Fragment 91-112 shows acetylation differences throughout the tested range, suggesting at least one of three lysine residues of this fragment (K95, K97, or K110) participates in the binding composition:TGF-beta 1 complex. To identify the lysine residue(s) involved, the chymotryptic digest is further treated with Glu-C producing two additional fragments 91-99 and 100-112. The later (fragment 100-112) contains K110, however, it shows no significant acetylation difference suggesting it is inaccessible either to solvent or to chemical modification.

The former (fragment 91-99) containing K95 and K97 is further tested using uncomplexed TGF-β1 treated with AHSE and MS/MS analysis to determine elution times of the singly-acetylated species, and to quantitate the extent of K95 or K97 acetylation (model data under such conditions are shown below in Table 8). Such data show that acetylation of K97 remains unchanged with or without complex formation, however, presence of an antibody composition of the invention significantly affects K95 acetylation indicating that K95 is directly involved in binding complex formation.

TABLE 7

Mole of Acetylated Amino Group per Mole Peptide Obtained by LC/MS for Epitope Mapping

| Ac. | | Mole of Acetylation/Mole peptide | | | | | | | | | | | |
|---|---|---|---|---|---|---|---|---|---|---|---|---|---|
| Time | Complex | 1-6 | 9-21 | 22-30 | 22-32 | 31-39 | 33-43 | 51-62 | 53-62 | 66-90 | 91-112 | 91-99 | 100-112 |
| 10 min | TGF β 1 + Cont. | 0.97 | 0.10 | 0.07 | 0.94 | 0.74 | 0.22 | 0.64 | 0.60 | 0.00 | 1.09 | 1.28 | 0.03 |
| | TGF β 1 + 21D1 | 0.95 | 0.09 | 0.07 | 0.95 | 0.78 | 0.26 | 0.50 | 0.45 | 0.00 | 0.49 | 0.71 | 0.02 |
| | TGFβ1 + DM4 * | 0.91 | 0.10 | 0.04 | 0.88 | 0.56 | 0.05 | 0.31 | 0.29 | 0.00 | 0.35 | 0.59 | 0.02 |
| | TGFβ1 + DM4 # | 0.91 | 0.07 | 0.06 | 0.92 | 0.62 | 0.13 | 0.30 | 0.28 | 0.00 | 0.39 | 0.66 | 0.02 |
| 20 min | TGF β 1 + Cont. | 1.00 | 0.25 | 0.14 | 0.99 | 0.89 | 0.35 | 0.82 | 0.79 | 0.00 | 1.32 | 1.57 | 0.05 |
| | TGF β 1 + 21D1 | 1.00 | 0.27 | 0.15 | 1.00 | 0.95 | 0.42 | 0.76 | 0.71 | 0.00 | 1.01 | 0.96 | 0.04 |
| | TGFβ1 + DM4 * | 1.00 | 0.23 | 0.06 | 0.95 | 0.76 | 0.09 | 0.52 | 0.51 | 0.00 | 0.55 | 0.81 | 0.03 |
| | TGFβ1 + DM4 # | 1.00 | 0.21 | 0.12 | 0.97 | 0.85 | 0.22 | 0.59 | 0.58 | 0.00 | 0.63 | 0.88 | 0.04 |
| 60 min | TGFβ1 + Cont. | 0.97 | 0.67 | 0.30 | 1.03 | 1.03 | 0.56 | 0.87 | 0.82 | 0.00 | 1.68 | 1.85 | 0.10 |
| | TGF β 1 + 21D1 | 0.97 | 0.79 | 0.36 | 1.08 | 1.21 | 0.73 | 0.93 | 0.92 | 0.00 | 1.24 | 1.39 | 0.08 |
| | TGF β 1 + DM4 * | 0.91 | 0.80 | 0.16 | 0.99 | 0.95 | 0.26 | 0.85 | 0.80 | 0.00 | 0.91 | 1.13 | 0.08 |
| | TGFβ1 + DM4 # | 0.99 | 0.66 | 0.36 | 1.06 | 1.10 | 0.51 | 0.93 | 0.91 | 0.00 | 1.14 | 1.25 | 0.09 |

* and # indicates the two different lots of the DM4 antibody are characterized separately.

TABLE 8

| Acetylation of K95 & K97 | | | |
|---|---|---|---|
| Acetylation Time | TGFb1 & Antibody Complex | Acetylation (%) | |
| | | K97 | K95 |
| 10 min | TGF-β1 + Control | 54 | 73 |
| | TGF-β1 + LA307-21D1 | 51 | 20 |
| | TGF-β1 + LA307-DM4* | 44 | 16 |
| | TGF-β1 + LA307-DM4# | 46 | 18 |
| 20 min | TGF-β1 + Control | 71 | 86 |
| | TGF-β1 + LA307-21D1 | 66 | 27 |
| | TGF-β1 + LA307-DM4* | 59 | 22 |
| | TGF-β1 + LA307-DM4# | 63 | 25 |
| 60 min | TGF-β1 + Control | 87 | 95 |
| | TGF-β1 + LA307-21D1 | 86 | 53 |
| | TGF-β1 + LA307-DM4* | 75 | 38 |
| | TGF-β1 + LA307-DM4# | 82 | 42 |

* and # indicate that two different lots of the DM4 antibody are characterized H/D exchange.

H/D exchange.

In epitope mapping, the technique of deuterium/hydrogen (H/D) exchange resembles protein surface labeling/MS, however, H/D exchange is not residue-specific, and thus can detect changes in any amino acid residue. In comparing a binding composition:TGF-beta 1 complex to an uncomplexed mature TGF-β1 protein, the molecular weight of the complexed protein is about 20 Da (or 30 Da at 100% $D_2O$) lower than uncomplexed TGF-β1 thus, by calculating $D_2O$ weight differences between complexed and uncomplexed TGF-β1, it can be shown that approximately thirty amino acid residues in the mature TGF-β1 dimer may participate in forming an invention binding complex.

120 μg aliquots (~140 or 280 μL) of antibody solutions are buffer exchanged into PBS by successive concentration and dilution using a Microcon (30 kD) ultrafiltration protein concentrator (Millipore). After two successive concentrations and dilutions with PBS, the antibody solutions are concentrated, removed, adjusted to a final volume 70 μL with PBS. Then, 10 μL of 1 mg/mL TGF-β1 in 4 mM HCl solution and 2 μL of 1 M tris buffer, pH 8.0, is added into each antibody vial to form a TGF-β1:antibody complex. A TGF-β1 control sample is prepared by mixing 70 μL of 1×PBS, 20 μL of TGF-β1 1 in 4 mM HCl solution, and 2 μL of 1 M tris buffer, pH 8.0. Subsequently, 9 μL of TGF-β1 or the TGF-β1 antibody complex is transferred into a micro plastic vial, and then 21 μL of 100% $D_2O$ is added to form a 70% $D_2O$ solution. The solution is incubated at ambient temperature for 10 min and then at 0° C. for 1 min.

After incubation, H/D exchange is quenched and the protein digested by adding 15 μL of 1% formic acid solution (at 0° C.) and 4 μL of 2 mg/mL pepsin solution (at 0° C.), and then incubating at 0° C. for 5 min. The digest is immediately injected onto the column manually for LC/MS analysis (as described above, except that the tubing and HPLC column are immersed in an ice-water bath).

Mature TGF-β1 resists pepsin digestion at low pH (~2.5) and low temperature (0° C.) due to disulfide bond formation. As a result, few cleavage peptides are produced and most of TGF-β1 is still intact despite longer digestion times and higher enzyme:protein concentrations. Identifiable TGF-β1 proteolytic fragments are typically generated at C-terminal and middle regions of the protein (e.g., fragments 58-64 or 61-64). Model data for the change in mass (delta mass) after D/H exchange using such fragments is shown below in Table 9. The delta mass for fragment 61-64 is approximately zero while the delta mass for fragment 58-64 is about 1 Da suggesting that the region protected from deuterium exchange—after complex formation with a binding composition of the invention—comprises amino acid residues 58-61.

TABLE 9

| Delta Masses of the Identified Peptic Peptide of TGF-beta 1 After D/H Exchange | | | | | | |
|---|---|---|---|---|---|---|
| Delta Mass | Peptic Peptide of TGF-β1 | | | | | |
| (100% $D_2O$)* | 61-64 | 59-64 | 58-64 | 58-61 | 91-104 | 90-104 |
| Average for DM4 (n = 3) | 0.04 | −0.87 | −1.02 | −0.30 | −1.85 | −1.87 |
| SD for DM4 (n = 3) | 0.01 | 0.11 | 0.21 | 0.05 | 0.30 | 0.30 |
| for 21D1 (n = 1) | 0.01 | −0.34 | −0.99 | −0.18 | −1.90 | −1.51 |

TGF-betal Mutagenesis

| | | |
|---|---|---|
| | | 1 … 50 |
| TGFb1 (normal) | (1) | ALDTNYCFSSTEKNCCVRQLYIDFRKDLGWKWIHEPKGYHANFCLGPCPY |
| TGFb1 (mutein) | (1) | ALDTNYCFSSTEKNCCVRQLYIDFKRDLGWKWVHEPKGYHANFCLGPCPY |
| | | 51 … 100 |
| TGFb1 (normal) | (51) | IWSLDTQYSKVLALYNQHNPGASAAPCCVPQALEPLPIVYYVGRKPKVEQ |
| TGFb1 (mutein) | (51) | IWSLDTQYSKVLALYNQHNPGASAAPCCVPQALEPLTILYYVGRTPKVEQ |
| | | 101 … 113 |
| TGFb1 (normal) | (101) | LSNMIVRSCKCS-[SEQ ID NO: 1] |
| TGFb1 (mutein) | (101) | LSNMIVRSCKCS-[SEQ ID NO. 144] |

To further define epitopes for binding compositions of the invention, traditional mutagenesis techniques are used to identify TGF-beta 1 residues critical in forming binding complexes with compositions of the invention. The crystal structure of the TGF-beta 3/TGF-beta RII complex (2002 Nat Struct Biol. 3:203-8) is used as a model to define significant TGF-beta 1 protein mutagenesis sites -R25K, K26R, V331, P87T, V89L, and K95T (shown above).

Ability to bind the TGF-beta 1 mutein is tested using binding compositions specific for TGF-beta isoforms and commercially available mAbs (ID11 and 240; R&D Systems), which prevent binding of TGF-beta 1 to its cognate receptor (TGF-beta RII). Testing is carried out in a laser-induced desorption/ionization time-of-flight mass spectrometer analysis.

Test mAbs, such as, e.g., mAb 3821 and 2471, which specifically bind TGF-beta 1 (disclosed in PCT/US2004/018921; US 60/485,820) and controls, such as, e.g., mAb1D11, which binds all three TGF-beta isoforms, are mixed (providing an opportunity to complex with the TGF-beta 1 protein (either mutein or wild-type)), immobilized on detecting chips, lazed, and subsequently analyzed using standardized software under manufactures conditions (Ciphergen Diagnostics).

Model results show that a distinct subset of amino acid residues at the binding interface of TGF-beta 1/TGF-beta RII differ from the other TGF-beta isoforms (TGF-beta 2, and TGF-beta 3. Test mAb #2471 (with specific binding affinity for TGF-beta 1) binds wild type TGF-beta 1 at a five-fold greater rate than the TGF-beta 1 mutein, while mAbs 3821, and ID11 bind the TGF-beta 1 mutein at a rate that is two and one-half fold less then wild type TGF-beta 1.

What is claimed is:

1. An antibody, or an antigen-binding fragment thereof, comprising:
    a light chain variable region having the amino acid sequence shown in SEQ ID NO: 43 and a heavy chain variable region having the amino acid sequence shown in SEQ ID NO: 90, or
    a light chain variable region having the amino acid sequence shown in SEQ ID NO: 146 and a heavy chain variable region having the amino acid sequence shown in SEQ ID NO: 117.

2. The antibody of claim 1, comprising:
    a light chain having the amino acid sequence shown in SEQ ID NO: 135 and a heavy chain having the amino acid sequence shown in SEQ ID NO: 134, or
    a light chain having the amino acid sequence shown in SEQ ID NO: 132 and a heavy chain having the amino acid sequence shown in SEQ ID NO: 133.

3. A pharmaceutical composition, comprising said antibody of claim 2 and a pharmaceutically acceptable carrier, diluent, or excipient.

4. The pharmaceutical composition of claim 3, wherein said antibody is present in an amount of from about 20 to about 100 mg/ml.

5. The pharmaceutical composition of claim 3, wherein said antibody comprises a light chain having the amino acid sequence shown in SEQ ID NO: 135 and a heavy chain having the amino acid sequence shown in SEQ ID NO: 134.

6. The pharmaceutical composition of claim 3, wherein said antibody comprises a light chain having the amino acid sequence shown in SEQ ID NO: 132 and a heavy chain having the amino acid sequence shown in SEQ ID NO: 133.

7. The pharmaceutical composition of claim 3, comprising a surfactant.

8. The pharmaceutical composition of claim 7, wherein said surfactant is polysorbate 80.

9. The pharmaceutical composition of claim 8, wherein said polysorbate 80 is present in an amount of from about 0.005% to about 0.05% by weight.

10. The pharmaceutical composition of claim 3, comprising a citrate buffer at a pH range of from about 5.5 to about 7.0.

11. The pharmaceutical composition of claim 10, wherein said citrate buffer is present in a concentration of about 10 mM sodium citrate at a pH range of from about 5.5 to about 7.0.

12. The pharmaceutical composition of claim 11, wherein said pH is about 6.0 to about 6.5.

13. The pharmaceutical composition of claim 3, comprising about 50 to about 150 mM sodium chloride.

* * * * *